United States Patent [19]

Ui et al.

[11] Patent Number: 5,000,953
[45] Date of Patent: Mar. 19, 1991

[54] BIOLOGICALLY ACTIVE SUBSTANCE

[75] Inventors: Michio Ui, Sapporo; Motoyuki Yajima; Chikanori Tomioka, both of Ohtsu; Koichi Hosoda, Shiga, all of Japan

[73] Assignee: Kaken Chemical Co., Ltd., Tokyo, Japan

[21] Appl. No.: 327,382

[22] Filed: Mar. 23, 1989

Related U.S. Application Data

[63] Continuation of Ser. No. 933,353, Nov. 19, 1986, abandoned, which is a continuation of Ser. No. 321,485, Nov. 16, 1981, abandoned, which is a continuation-in-part of Ser. No. 132,789, Mar. 24, 1980, abandoned, which is a continuation-in-part of Ser. No. 870,120, Jan. 17, 1978, abandoned.

[30] Foreign Application Priority Data

Feb. 1, 1977 [JP] Japan .................................. 52-10397

[51] Int. Cl.$^5$ ......................... A61K 35/72; C12P 1/02
[52] U.S. Cl. ..................................... 424/115; 435/171
[58] Field of Search ......................... 424/115; 435/171

[56] References Cited

PUBLICATIONS

Bergery's Manual of Determinative Bacteriology, vol. 8, pp. 282–283 (1974).
"Cell–Envelope Proteins of *Bordetella pertussis*", Parton et al., J. Med. Microbiol., vol. 8, pp. 47–56 (1975).
The American Type Culture Collection, Catalog of Strains, p. 19 (1970).
Morse et al., J. of Experimental Medicine, vol. 143, 1976, pp. 1483–1502.
Lehrer et al, J. of Immunology, vol. 113, No. 1, 7/74, pp. 18–27.
Arai et al., Biochimica et Biophysica Acta, 444, 1976, 765–782.
Chemical Abstracts, 71: 68911(u) (1969).

*Primary Examiner*—Allen J. Robinson
*Attorney, Agent, or Firm*—Wegner, Cantor, Mueller & Player

[57] ABSTRACT

A novel biologically active substance named Islets-Activating Protein obtained from the cultivation of the miocroorganism Bordetella and having insulin secretion promoting action as well as glucose tolerance improving action for mammals.

10 Claims, 18 Drawing Sheets

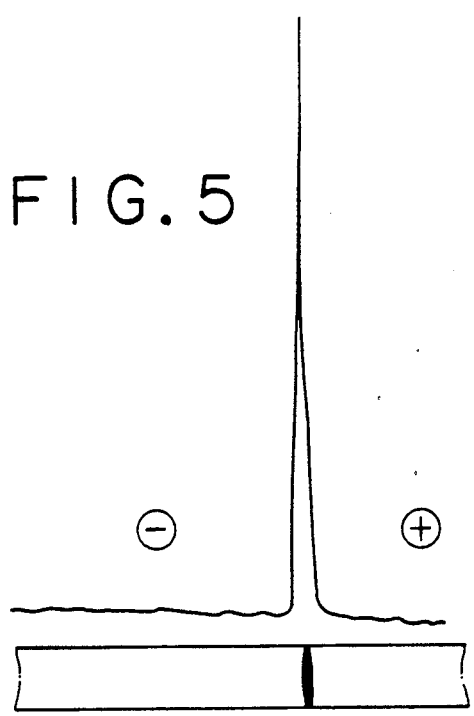
FIG. 5 ELECTROPHORETIC PATTERN OF IAP
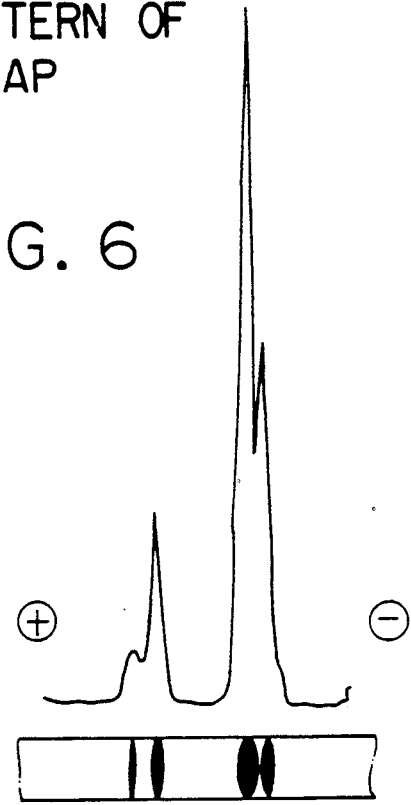
FIG. 6 SDS-ELECTROPHORETIC PATTERN OF IAP
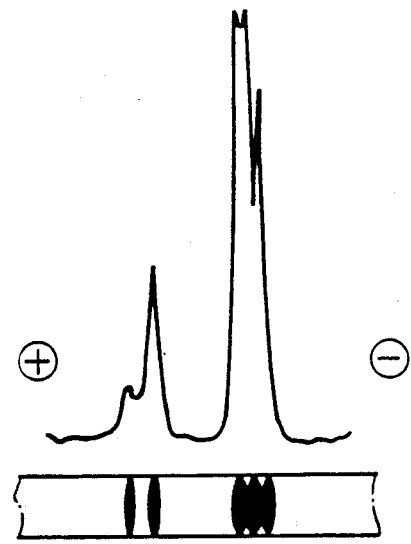
FIG. 7 SDS-ELECTROPHORETIC PATTERN OF IAP

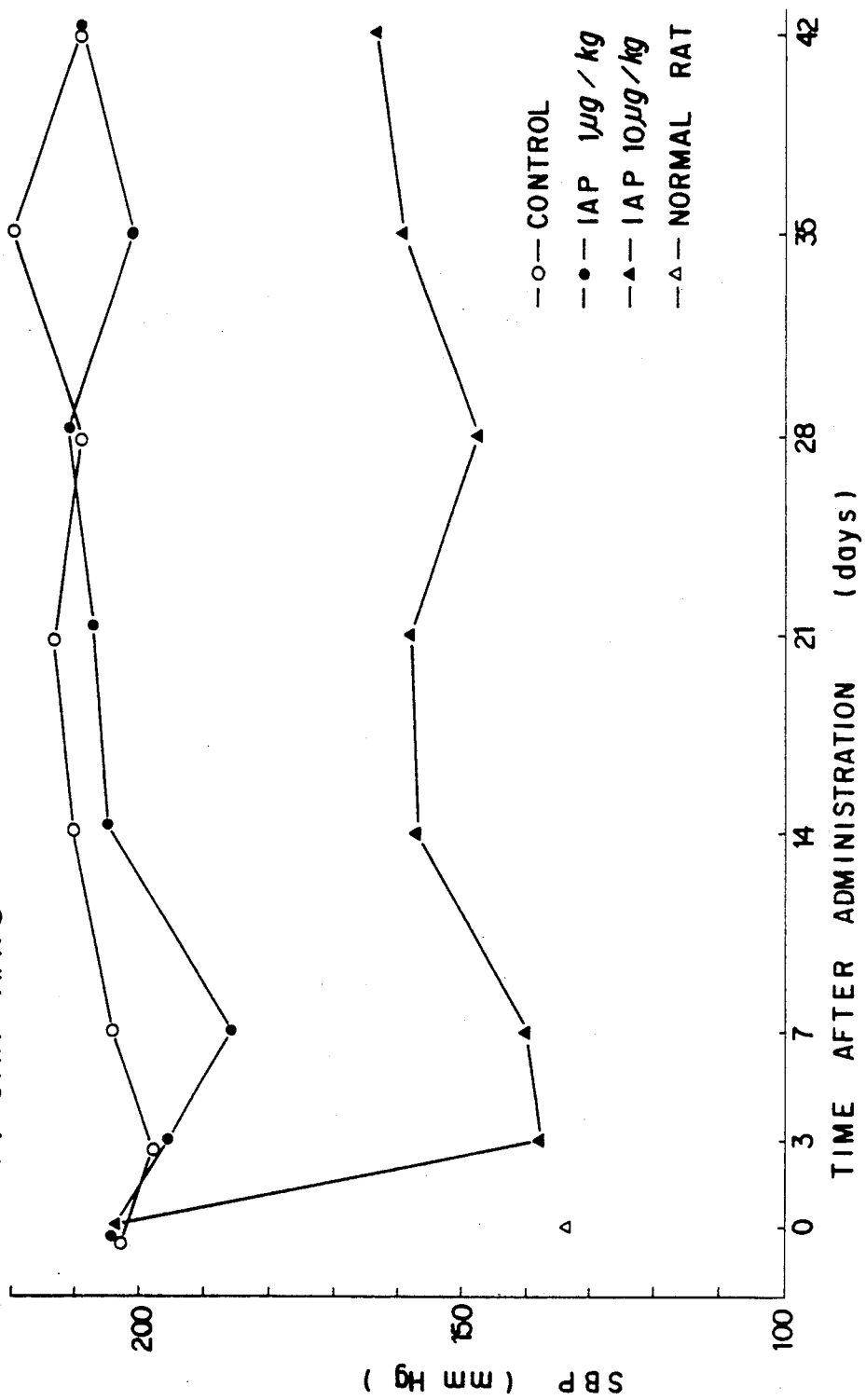

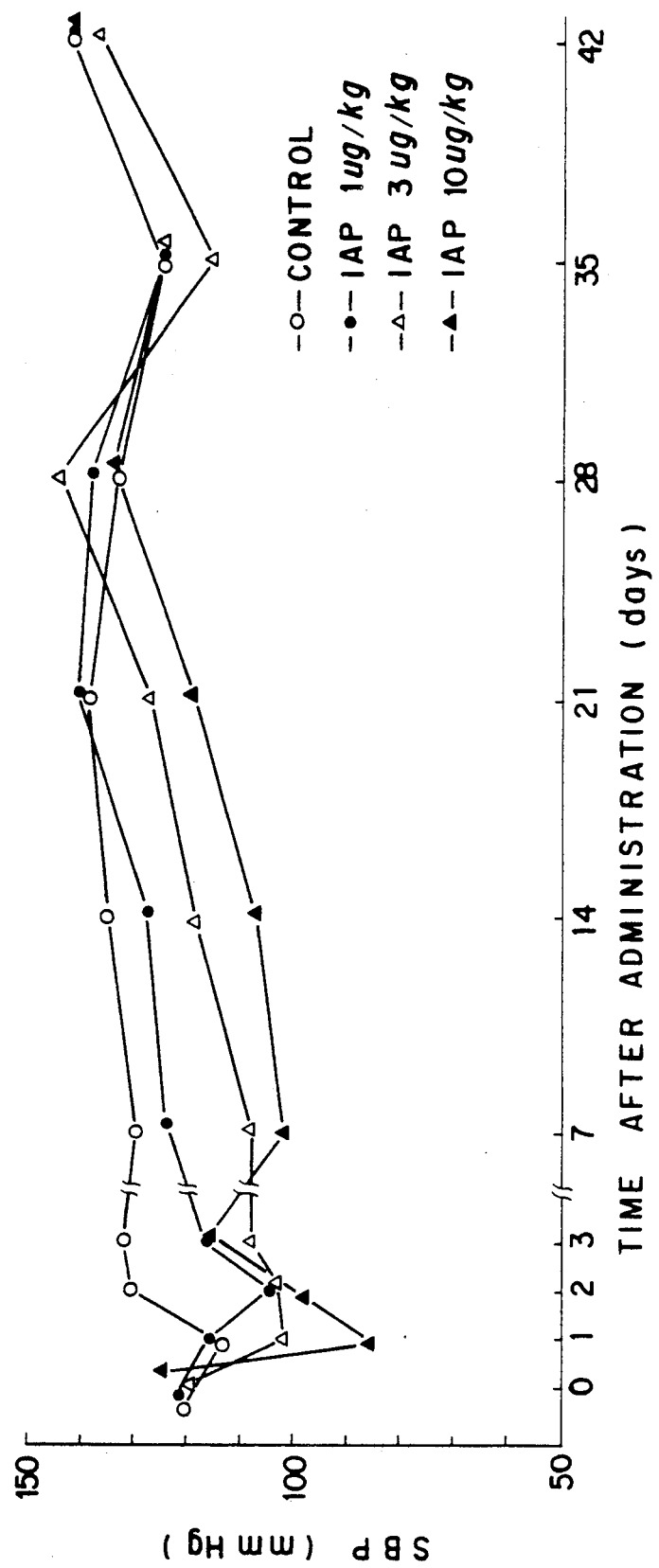
FIG. 20 EFFECT OF IAP ON SYSTOLIC BLOOD PRESSURE IN NORMAL RATS

BIOLOGICALLY ACTIVE SUBSTANCE

CROSS-REFERENCE TO RELATED APPLICATIONS:

The present application is a continuation of application Ser. No. 06/933,353, filed Nov. 19, 1986 (abandoned), which is a continuation of application Ser. No. 06/321,485, filed Nov. 16, 1981 (abandoned), which is a continuation-in-part of application Ser. No. 06/132,789, filed Mar. 24, 1980 (abandoned), which is a continuation-in-part of application Ser. No. 05/870,120, filed Jan. 17, 1978 (abandoned).

SUMMARY OF THE INVENTION:

In a first aspect of the invention, there is provided a biologically active substance referred to herein as Islets-Activating Protein having insulin secretion promoting action obtained from the cultivation of strains of the microorganism Bordetella pertussis, said substance having the following properties:

a molecular weight of 73,000±11,000 as determined by gel filtration;

a protein content as determined by Lowry's method being not less than 95% by weight;

the glucide content by the phenol-$H_2SO_4$ method being less than 2% by weight;

the lipid content being lower than the limit of detection;

percentile amino acid composition of the protein moiety (average ratio, μM/100 μM) being: aspartic acid, 7.5-7.9; threonine, 6.8-7.8; serine, 5.9-7.6; glutamic acid proline, 5.5-6.4; glycine, 8.7-9.6; alanine, 9.0-10.8; cystine/2, 1.0-2.5; valine, 6.5-7.6; methionine, 2.5-3.3; isoleucine, 3.6-4.6; leucine, 7.4-8.7; tyrosine, 5.1-6.8; phenylalanine, 3.7-4.5; lysine, 3.1-4.4; histidine, 0.9-1.5; and arginine, 6.1-6.6;

disc electrophoretic pattern: acrylamide (polyacrylamide concentration, 7.5%; a 1N KOH-glacial acetic acid buffer (pH 4.3)) disc electrophoresis of said substance giving a very sharp single band on the cathode side;

hydroxyapatite column chromatographic pattern: said substance in 0.1 M phosphate buffer (pH 7.0) being adsorbed on said column and the adsorbed substance being eluted with 0.1M phosphate buffer (pH 7.0) containing 0.5M NaCl;

isoelectric point of pH 8.9±0.5;

optical rotation $[\alpha]_D^{25} = -29° \pm 5°$; and said substance having insulin secretion promoting activity not less than 193 units/μg as well as glucose tolerance improving action for mammals.

In a second aspect of the invention, there is provided an anti-diabetic composition in dosage unit form, which comprises an anti-diabetically effective amount of a biologically active substance referred to herein as Islets-Activating Protein having insulin secretion promoting action, obtained from the cultivation of at least one strain of the microorganism Bordetella pertussis, said substance having the following properties:

a molecular weight of 73,000±11,000 as determined by gel filtration;

a protein content as determined by Lowry's method being not less than 95% by weight;

the glucide content by the phenol-$H_2SO_4$ method being less than 2% by weight;

the lipid content being lower than the limit of detection;

percentile amino acid composition of the protein moiety (average ratio, μM/100 μM) being: aspartic acid, 7.5-7.9; threonine, 6.8-7.8; serine, 5.9-7.6; glutamic acid, 8.8-10.0; proline, 5.5-6.4; glycine, 8.7-9.6; alanine, 9.0-10.8; cystine/2, 1.0-2.5; valine, 6.5-7.6; methionine, 2.5-3.3; isoleucine, 3.6-4.6; leucine, 7.4-8.7; tyrosine, 5.1-6.8; phenylalanine, 3.7-4.5; lysine, 3.1-4.4; histidine, 0.9-1.5; and arginine, 6.1-6.6;

disc electrophoretic pattern: acrylamide (polyacrylamide concentration, 7.5%, a 1N KOH-glacial acetic acid buffer (pH 4.3)) disc electrophoresis of said substance giving a very sharp single band on the cathode side;

hydroxyapatite column chromatographic pattern: said substance in 0.1 M phosphate buffer (pH 7.0) being adsorbed on said column and the adsorbed substance being eluted with 0.1 M phosphate buffer (pH 7.0) containing 0.5 M NaCl;

isoelectric point of pH 8.9±0.5;

optical rotation $[\alpha]_D^{25} = -29° \pm 5°$; and, said substance having insulin secretion promoting activity not less than 193 units/μg as well as glucose tolerance improving action for mammals; and a pharmaceutically acceptable carrier therefor.

In a third aspect of the invention, there is provided a method of treating a patient suffering from diabetes which comprises administering to said patient an anti-diabetically effective amount of a biologically active substance referred to herein as Islets-Activating Protein having insulin secretion promoting action, obtained from the cultivation of strains of the microorganism Bordetella pertussis, said substance having the following properties;

a molecular weight of 73,000±11,000 as determined by gel filtration;

a protein content as determined by Lowry's method being not less than 95% by weight;

the glucide content by the phenol-$H_2SO_4$ method being less than 2% by weight;

the lipid content being lower than the limit of detection;

percentile amino acid composition of the protein moiety (average ratio, μM/100 μM) being: aspartic acid, 7.5-7.9; threonine, 6.8-7.8; serine, 5.9-7.6; glutamic acid, 8.8-10.0; proline, 5.5-6.4; glycine, 8.7-9.6; alanine, 9.0-10.8; cystine/2, 1.0-2.5; valine, 6.5-7.6; methionine, 2.5-3.3; isoleucine, 3.6-4.6; leucine, 7.4-8.7; tyrosine, 5.1-6.8; phenylalanine, 3.7-4.5; lysine, 3.1-4.4; histidine, 0.9-1.5; and arginine, 6.1-6.6;

disc electrophoretic pattern: acrylamide (polyacrylamide concentration, 7.5%; a 1N KOH-glacial acetic acid buffer (pH 4.3)) disc electrophoresis of said substance giving a very sharp single band on the cathode side;

hydroxyapatite column chromatographic pattern: said substance in 0.1 M phosphate buffer (pH 7.0) being adsorbed on said column and the adsorbed substance being eluted with 0.1 M phosphate buffer (pH 7.0) containing 0.5 M NaCl;

isoelectric point of pH 8.9±0.5;

optical rotation $[\alpha]_D^{25} = -29° \pm 5°$; and, said substance having insulin secretion promoting activity not less than 193 units/μg as well as glucose tolerance improving action for mammals.

In a fourth aspect of the invention, there is provided a process for preparing a biologically active substance having insulin secretion promoting activity not less than 193 units/μg as well as glucose tolerance improving action for mammals, which comprises culturing a pathogenic strain of the microorganism *Bordetella pertussis* in a culture medium therefor and recovering from the cultured cells and/or culture medium said substance having insulin secretion promoting activity for mammals, by at least one selected from the group consisting of the chromatographic method, the molecular sieve method, the electrophoretic method and the biological method.

In a fifth aspect of the invention, there is provided a biologically active substance referred to herein as Islets-Activating Protein having insulin secretion promoting action not less than 193 units/μg as well as glucose tolerance improving action for mammals, obtained by culturing a pathogenic strain of the microorganism *Bordetella pertussis* in a culture medium therefor and recovering from the cultured cells and/or culture medium said substance having insulin secretion promoting activity for mammals.

BACKGROUND OF THE INVENTION:

The present invention relates to a biologically active substance and the process for preparing and isolating a therapeutically valuable substance and more particularly, to the biologically active substance having insulin secretion promoting action and the process for preparing a substance obtained from the cultivation of suitable strains of a microorganism, *Bordetella pertussis* (Phase I or Phase II) in a suitable culture medium, and to the thus obtained substance.

The present inventors have detected in the cells and in their culture medium of Bordetella pertussis known as the pathogen of pertussis, a proteinic substance having the amazing pharmacological activities in promoting the secretion of insulin thus resulting in maintaining the normal blood sugar level in mammals, and which, accordingly, is credited with a high medical utility for treatment and prevention of various kinds of diabetes. The present inventors have also succeeded in isolation and chemical identification of this novel proteinic substance as an insulin secretion potentiating factor and after finding that the proteinic substance demonstrates a prominent activity in promoting the secretion of insulin at an extremely small dose of approximately 0.1 μg/kg body weight, have proved usefulness in treatment and prevention of various kinds of diabetes, and then have attained to the present invention.

BRIEF DESCRIPTION OF THE DRAWINGS:

FIGS. 5 to 7 are schematic representations of electrophoretic pattern of IAP, SDS-electrophoretic pattern of IAP, and SDS-electrophoretic pattern of IAP respectively.

FIG. 19 is a graphic representation of an effect of IAP on systolic blood pressure in SHR rats.

FIG. 20 is a graphic representation of an effect of IAP on systolic blood pressure in normal rats.

Figure 1:
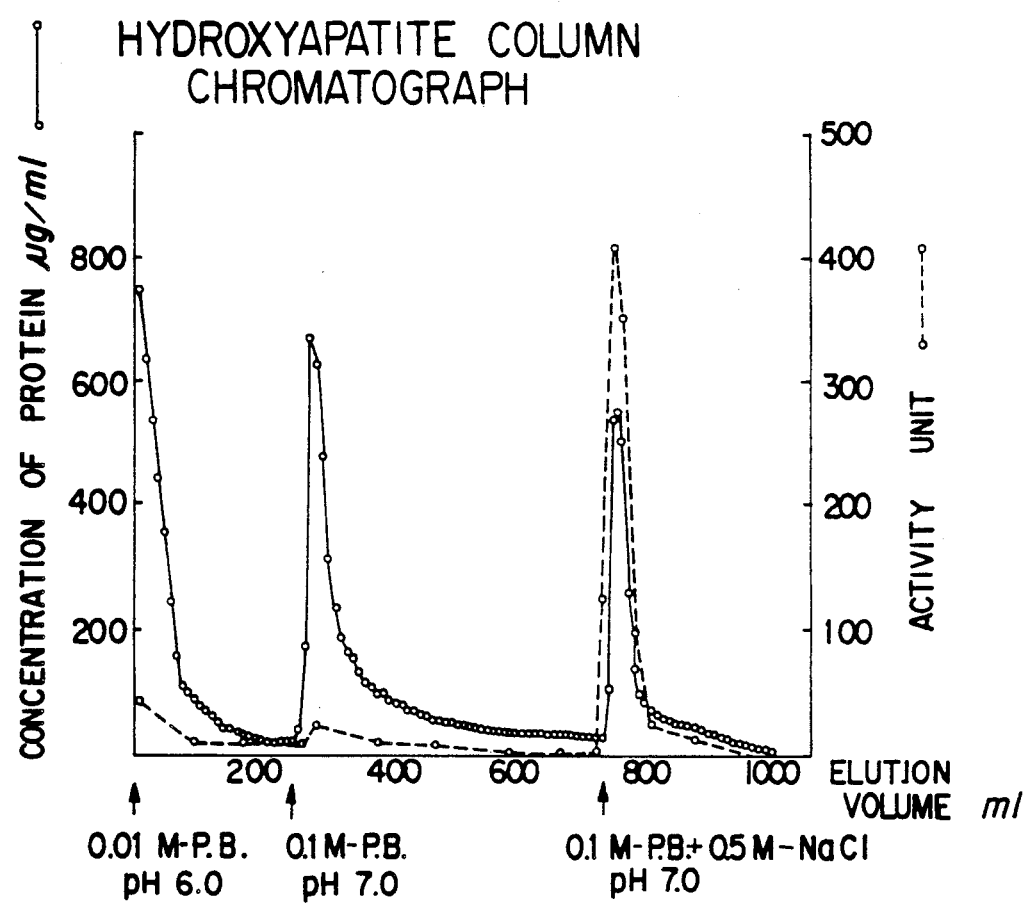
FIGS. 1 to 4 are graphic representations of hydroxyapatite column chromatography, carboxymethyl sepharose CL-6B column chromatography, Con A-sepharose column chromatography, and Biogel P-100 column chromatography respectively.

DETAILED DESCRIPTION OF THE INVENTION:

The proteinic substance having an activity of promoting the secretion of insulin (hereinafter abbreviated and referred to as IAP which means Islets-Activating Protein) is a substance which can be obtained by culturing the microorganism of *Bordetella pertussis* (Phase I or Phase II), most preferably *Bordetella pertussis* (Phase I) in a solid or liquid culture medium and after collecting crude product from the cultured bacterial cells and/or the culture medium, purifying the thus obtained crude product.

Collection and purification of the crude product to obtain IAP from the culture can be accomplished in general by one or combination of the methods of column chromatography, dialysis, electrophoresis, gel-filtration, ion-exchange, fractional precipitation, extraction with solvent and molecular sieve, and accordingly, the present invention is not defined by any specific methods for collection and purification.

As an example of the highly advantageous methods for collecting and purifying the crude product to obtain IAP, a column chromatographic process is suggested as shown below. According to this process, the supernatant of the culture medium of the bacteria is passed through a column filled with Hydroxyapatite column, Haptoglobin Sepharose (trademark for bead formed agarose gel) column, Carboxymethyl Sepharose column such as Carboxymethyl Sepharose CL-6B column (made by Pharmacia Fine Chemicals. Inc.), Sephacryl (trademark for covalently cross-linked sephacryl allyl dextran/N,N' methylene bisacrylamide) (S-200) column, Concanavalin Sepharose column such as Con A-Sepharose column (made by Pharmacia Fine Chemicals. Inc.), Biogel (trademark for copolymerized acrylamide/N,N'-methylene-bis-acrylamide) (P-100) column, Biogel (P-150) column p-Acetoxymercurianiline Sepharose column such as p-Acetoxymercurianiline Sepharose 6 MB column or Anti-IAP antibody-Sepharose column such as Anti-IAP antibody-Sepharose 4B column to adsorb IAP. The adsorbed IAP is eluted from the column-material with a suitably selected elutant such as aqueous Tris-hydrochloric acid solution containing KNCS, aqueous phosphate buffer solution containing urea or aqueous phosphate buffer containing sodium chloride. By applying dialysis to the thus eluted solution, unnecessary salts are removed to obtain a fraction containing IAP.

Since, IAP is also present in the cultured bacterial cells, according to the necessity, IAP may be collected therefrom by, for example, adding sodium chloride to the aqueous suspension of the cells to leach out IAP into the aqueous solution.

The so-called precipitation method by ammonium sulfate popularly used in the art is also applicable for preparation of IAP. In this case, solid ammonium sulfate is added to the supernatant of the culture medium of the bacteria to a point approximate to saturation and the pH of the mixture is adjusted to 6 to 7 with a dilute ammonia liquor. Then, the thus obtained precipitate was separated and washed with water, and then IAP was extracted with aqueous 0.1 M tris-buffer solution of pH 8 containing sodium chloride at 0.5 M to obtain a solution of IAP.

Although *Bordetella pertussis* produces IAP as has been described above, its various mutants obtained by the conventional method for causing mutation of the bacteria, such as modification of the components of culture medium, exposure of the bacteria to a radioactive irradiation such as ultraviolet rays, X-rays, etc. or use of a mutagenic agent, are also useful as a microorganism for producing IAP.

In addition, although the liquid-shaking culture method is preferable in viewpoints of the yield of IAP and its activity, other methods for culture may be used.

The mycological properties of and conditions for culturing the bacterial species belonging to the genus Bordetella are described in "Bergy's Manual of Determinative Bacteriology, 8th Ed.", (1974), Williams & Wilkins Co., Baltimore, Md., USA., "J. Exp. Med. ", Vol. 129, pages 523–550(1969) and "Saikingaku Jisshu Teiyo (Handbook for Mycological Training) 3rd Ed." (1972), Maruzen Co.

The chemical and physical properties of IAP are described below.

The powder of IAP obtained by freeze-drying the aqueous dialysed and de-salted solution is non-deliquescent, and white or light brown in colour, and is soluble in water to the extent of 3 to 5 mg/ml at room temperature. It is also soluble in pyridine, 2-mercaptoethanol and aqueous solution of sodium dodecylsulfate and of cystine. When IAP is put into aqueous 6N hydrochloric acid solution, a precipitate white in colour separates out. Addition of sodium sulfate, dry ice plus acetone, ethanol, trichloroacetic acid, aqueous solution of zinc chloride or aqueous solution containing other several kinds of metal ion to an aqueous solution of IAP at cold (4° C.), causes turbidity in the aqueous solution and a precipitate. When IAP is put into a mixture of water and chloroform or of water and n-butanol, IAP gathers on the interface of both liquids.

When an aqueous solution of IAP is heated to 80° C. or higher, the solution becomes turbid white in colour. In addition, when IAP is dissolved into aqueous 0.1 M phosphate buffer solution of pH of 7.0 containing sodium chloride at 0.5 M and the solution is subjected to dialysis against distilled water as the external liquid, the mixed solution becomes turbid once, however, with the progress of dialysis, the white turbidity disappears completely.

Molecular weight of IAP:

(i) The molecular weight of IAP determined by gel-filtration method using a column(2.8cm×80 cm) of Biogel P-100 (made by Bio. Rad. Co.) equilibrated by aqueous 0.1 M phosphate buffer solution containing sodium chloride at 0.5 M is 73,000±11,000.

(ii) After dissolving the active substance of the present invention into aqueous 0.01 M potassium dihydrogen phosphate buffer solution additionally containing 0.1 M of sodium chloride and 2 M of urea, the solution is subjected to an "Hitachi-ultracentrifuge for Analysis Model UCA-1" (made by Hitachi Works Co., Ltd. Japan) of 60,000 r.p.m. at 15° C. to obtain the molecular weight.

The thus obtained molecular weight of IAP determined by ultracentrifugal method is 116,000±7,000.

Component of IAP:

The content of protein in IAP determined by Lowry's method is not less than 95% by weight, and the content of glucide determined by phenol-sulfuric acid method is less than 2% by weight. The concentration of lipid in IAP was below the lower limit of detection.

The following literatures were referred to for measurement of the respective components:

Protein

Lowry, O. H., N. J. Rosebrough, A. L. Farr and R. J Randall: "J. Biol. Chem. ",193:265, 1951.

Glucide

Phenol-$H_2SO_4$ method. Dobois, M., K. A. Giles, J. K. Hamilton, P. A. Rebers and F. Smith: "Anal. Chem." 28 350, 1956.

Lipid

Total lipid and lipid conjugate were measured according to Marsh and Weinstein method (J. B. Marsh and D. B. Weinstein: J. Lipid Res., 7,574, 1966) by extracting the material before and after hydrolysis into chloroform, chloroform-methanol and heptane.

The amino acid composition of the protein component of IAP is determined according to Lowry, O. H. et al. "J. Biol Chem.",193 page 265 (1951), the result being as follows: (IAP was hydrolyzed in aqueous 6N hydrochloric acid at 110° C. for 24 hours at a concentration of $\mu M/100\ \mu M$).

Compositional ratio is aspartic acid of 7.5 to 7 9; threonine of 6.8 to 7.8; serine of 5.9 to 7.6; glutamic acid of 8.8 to 10.0; proline of 5.5 to 6.4; glycine of 8.7 to 9.6, alanine of 9.0 to 10.8; cystine/2 ff 1.0 to 2.5; valine of 6 5 to 7.6; methionine of 2.5 to 3.3; isoleucine of 3.6 to 4.6; leucine of 7.4 to 8.7; tyrosine of 5.1 to 6 8; phenylalanine of 3.7 to 4.5; lysine of 3.1 to 4.4; histidine of 0.9 to 1.5 and arginine of 6.1 to 6.6.

Isoelectric point of IAP:

The isoelectric point of IAP determined by the method described in Wringley, C. W., "J. Chromatogr.", 36, 362-372 (1968) is pH 8.9±0.5.

Optical rotation of IAP:

The optical rotation is $[\alpha]_D^{25} = -29\pm5°$.

Absorption of ultraviolet of IAP:

The absorption of ultraviolet is $\lambda_{max}277\pm3$ nm (log $\epsilon 4.79\pm0.3$)

Nuclear magnetic resonance spectrum of IAP:

The specific absorptions of nuclear magnetic resonance spectrum are 1.2–3.5 ppm, 4.0–6.0 ppm and 6.7–8.8 ppm.

Absorption of infrared of IAP:

The absorption of infrared refer to FIGS. 8 to 12, 14 17 and 18.

Sedimentation constant of IAP:

The sedimentation constant is 6.5±0.3 S.

Elementary Analysis of IAP (Found):

Carbon content is 46.6±6.2%, hydrogen content is 6.7±0.9%, nitrogen content is 14.4±1.2%, sulfur content is 1.7±0.4% and oxygen content is balance.

Disc electrophoretic pattern of IAP:

IAP is subjected to disc electrophoresis using polyacrylamide gel of concentration of 7.5% as the supporting body and aqueous 1N potassium hydroxide-acetic acid buffer solution of pH of 4.3 as the electrolyte solution under the conditions of 30 micrograms of specimen, applied current of 4 mA, duration of 2 hours/gel, staining by Amido-black 10B and destaining by aqueous 7% acetic acid solution to give an extremely sharp band at the distance of 2.3±0.2 cm from the end of spacer gel. The procedures are carried out the following description by J. V. Maizel, Jr. (refer to Biochem. Biophys. Res. Comm., 13, 483 (1963)).

Biological properties of IAP:

IAP has an activity of promoting the secretion of insulin not less than 193 unit/μg and an activity of improving the glucose tolerance in mammals, and these actions are maintained for several weeks to several months after a single administration of IAP.

Acute toxicity ($LD_{50}$, i.v.) to ddY mice is about 230 μg/kg body weight.

The present invention will be explained more in detail while referring to the following non-limitative examples of which Examples 1 to 11 show the preparation and the physical and chemical properties of IAP, and Examples 12 and 14 show the pharmacological properties of IAP.

EXAMPLE 1:

Lyophillized and preserved bacterial strain Tohama Phase I of *Bordetella pertussis*, (supplied by Department of Bacteriology, School of Pharmaceutical Sciences Kitasato University) showing the bacteriological properties agreeing with those of *Bordetella pertussis* Phase I described in the afore-mentioned literatures, was plate-cultured in Bordet-Gengou culture medium at 37° C. for 2 days, and a platinum-loopful of the bacterial colony was inoculated into 200 ml of a modified Cohen-Wheeler culture medium added with an ion-exchange resin (hereinafter referred to as CW medium) shown in Table 1 which was placed in a 500 ml-shaking flask, and subsequently subjected to shaking culture for 22 hours at 37° C. The thus precultured bacteria were inoculated into 1 liter of CW medium placed in each 2 liter-shaking flask at a rate of about $0.1 \times 10^9$ cells/ml of the medium (by determining the bacterial concentration with a spectrophotometer at a wave length of 650 nm), and subsequently subjected to shaking culture for 48 hours at 37° C. under a shaking rate of 97 times/min.

TABLE 1

| Composition of modified Cohen-Wheeler medium | |
|---|---|
| Casamino acid | 10 g |
| Yeast extract | 1 g |
| Potassium dihydrogenphosphate | 0.5 g |
| Soluble starch | 2 g |
| 0.5% copper sulfate solution | 1 ml |
| 1% calcium chloride solution | 1 ml |
| 4% magnesium chloride solution | 1 ml |
| Polypeptone | 5 g |
| 1% cystine solution | 2.5 ml |
| 0.5% iron sulfate solution | 1 ml |
| Sodium chloride | 2.5 g |

After adding distilled water to the composition to prepare an aqueous solution of a total volume of 1000 ml, and adjusting the pH of the solution to 7.2 by the addition of aqueous 20% sodium hydroxide solution, 3 g of an anion-exchange resin (Diaion SA-20 AP, made by Mitsubishi Kasei Co.) was added further to the solution and then the solution was autoclaved for 15 min. at 121° C. to be CW medium.

The thus obtained 48-hour shaking culture solution of the bacteria was heated for 30 min at 56° C. and then centrifuged at 15,000 r.p.m. at 4° C. to separate into the supernatant liquid and bacterial cells, the thus obtained supernatant being used as the starting material for obtaining IAP, the object product of the present invention by the following steps.

After adjusting the pH of 10 liters of the supernatant to 6.0 with the addition of aqueous 1N hydrochloric acid solution, the supernatant was poured into a hydroxyapatite column (2.5 cm × 40 cm) (made by Biochemical Industry Ltd.) at a rate of 200 ml/hour as the first step.

Most of proteins passed through the column without being adsorbed, and any activity of promoting the secretion of insulin could be scarcely detected. The determination of the concentration of protein was carried out according to the Lowry et al. method.

Then, after washing the column with a 0.01 M phosphate buffer solution of pH 6.0, and then 0.1 M phosphate buffer solution of pH 7.0 to elute the proteins other than IAP adsorbed onto the column, the fractions containing IAP was eluted with a 0.1 M phosphate buffer solution containing sodium chloride at 0.5 M, the fractions showing the identical pattern of proteins with that of IAP itself (refer to FIG. 1).

Figure 2:
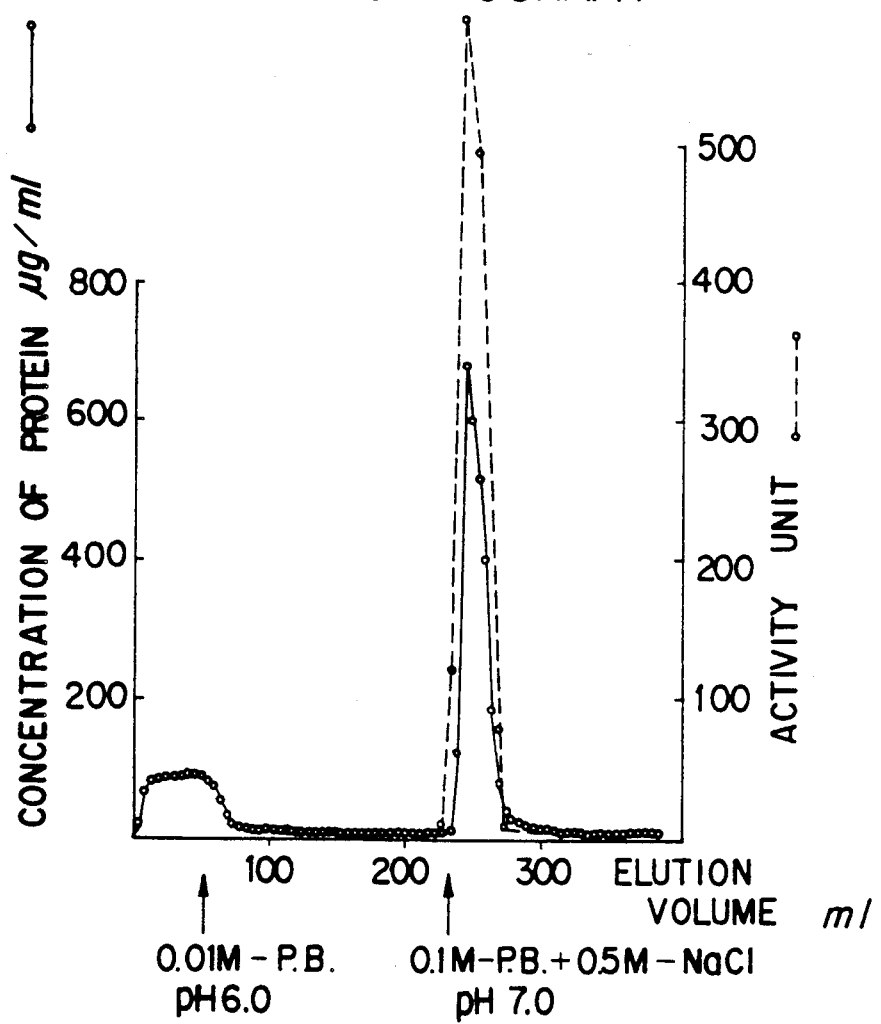

The thus eluted fractions containing IAP was condensed and dialysed two times using a membrane of the maximum permeated molecular weight of 8,000 (Catalogue No. 3787-F25, made by Thomas Co.) against distilled water as the external liquid for 12 hours (total), and then further dialysed two times using the same type of membrane, however, against 0.01 M phosphate buffer solution of pH 6.0 as the external liquid for 12 hours (total). The thus dialysed solution containing IAP was further purified by passing a column (1.5 cm × 10 cm) of Carboxymethyl Sepharose CL-6B, the column having been equilibrated with 0.01 M phosphate buffer solution. The materials not adsorbed onto this column showed no activity of promoting the secretion of insulin. Then, the column was washed with 0.1 M phosphate buffer of pH 7.0 containing sodium chloride at 0.5 M to collect the fractions. The thus collected fraction contained IAP showing the identical pattern of proteins with that of IAP itself (refer to FIG. 2).

Since the fraction still contained a minute amount of impurities detectable in disc electrophoresis, the fraction was condensed and subjected to dialysis against distilled water two times (total 12 hours) and further to dialysis against 0.01 M phosphate buffer solution of pH 7.0 two times (total 12 hours) while using the same membrane as mentioned above.

The dialysate was passed through a column (1.5 cm × 8 cm) of Con A-Sepharose 4B equilibrated with 0.01 M phosphate buffer solution.

Figure 3:
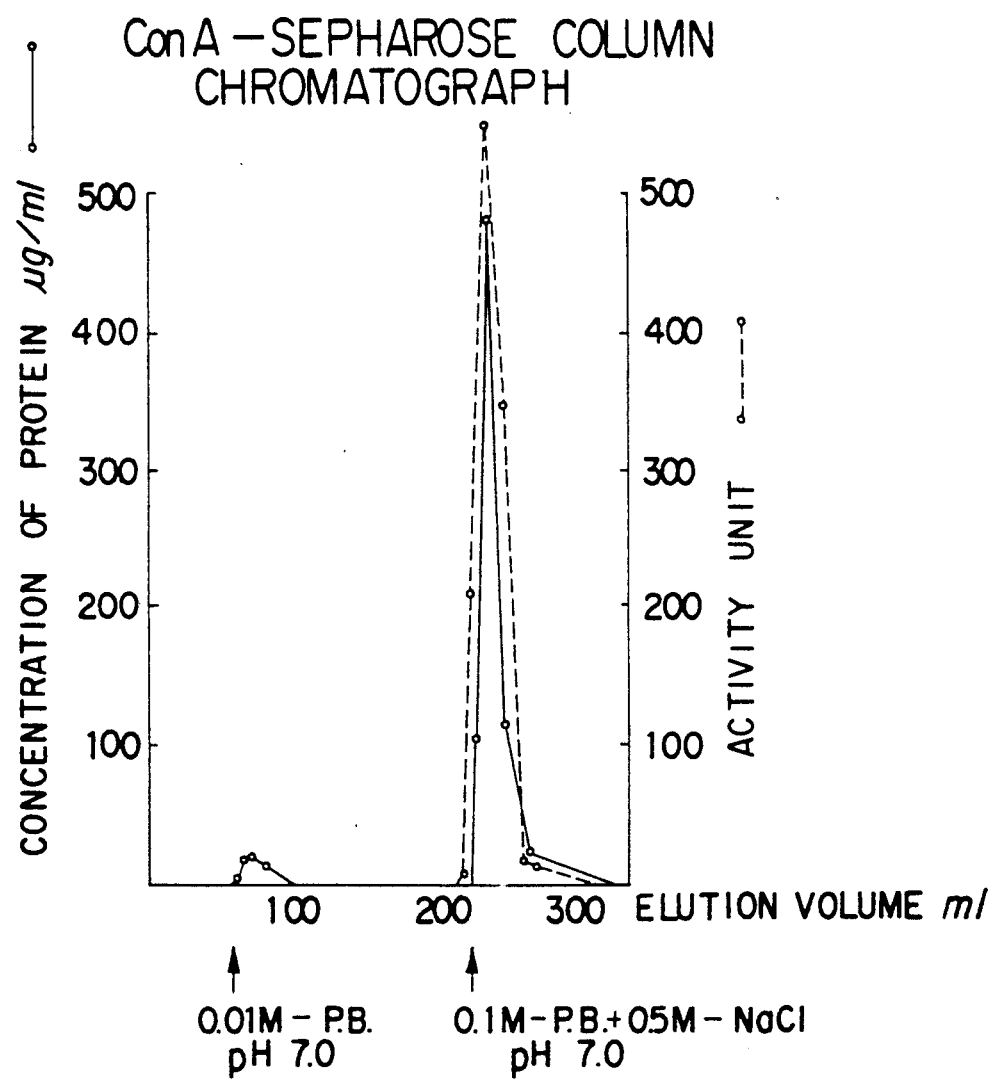

On eluting the column with 0.01 M phosphate buffer solution, although an eluate containing a minute amount of proteins was obtained the protein showed no activity of promoting the secretion of insulin, and accordingly the column was further eluted with 0.1 M phosphate buffer solution of pH 7.0 containing sodium chloride at 0.5 M to obtain the fraction containing proteins which showed the identical pattern to that of IAP (refer to FIG. 3).

Figure 4:
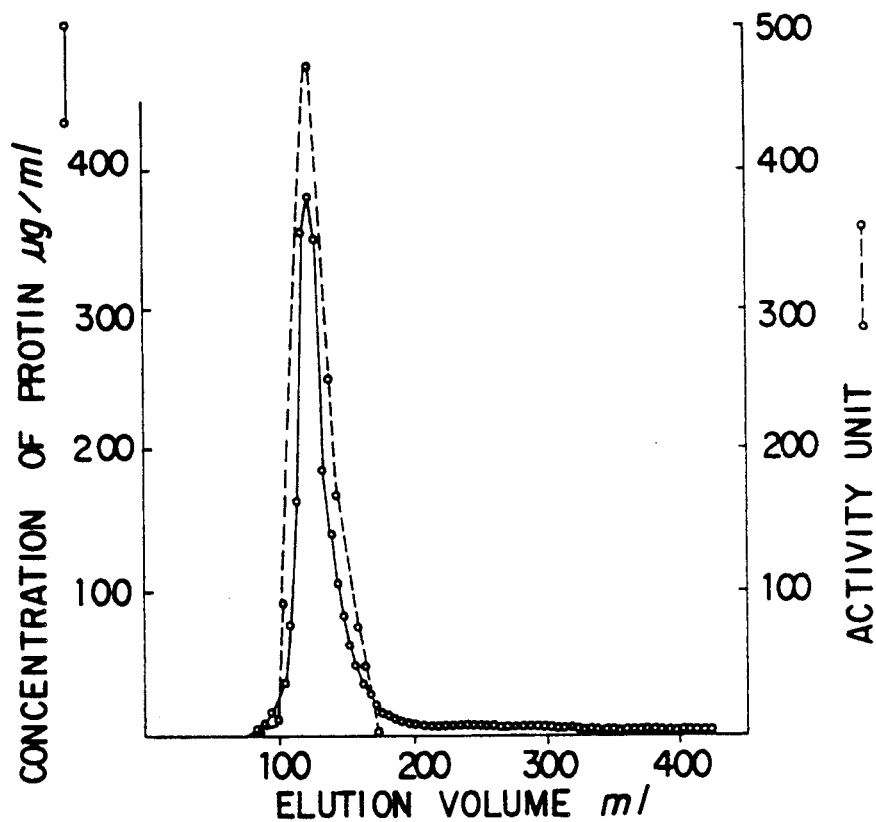
Figure 8:
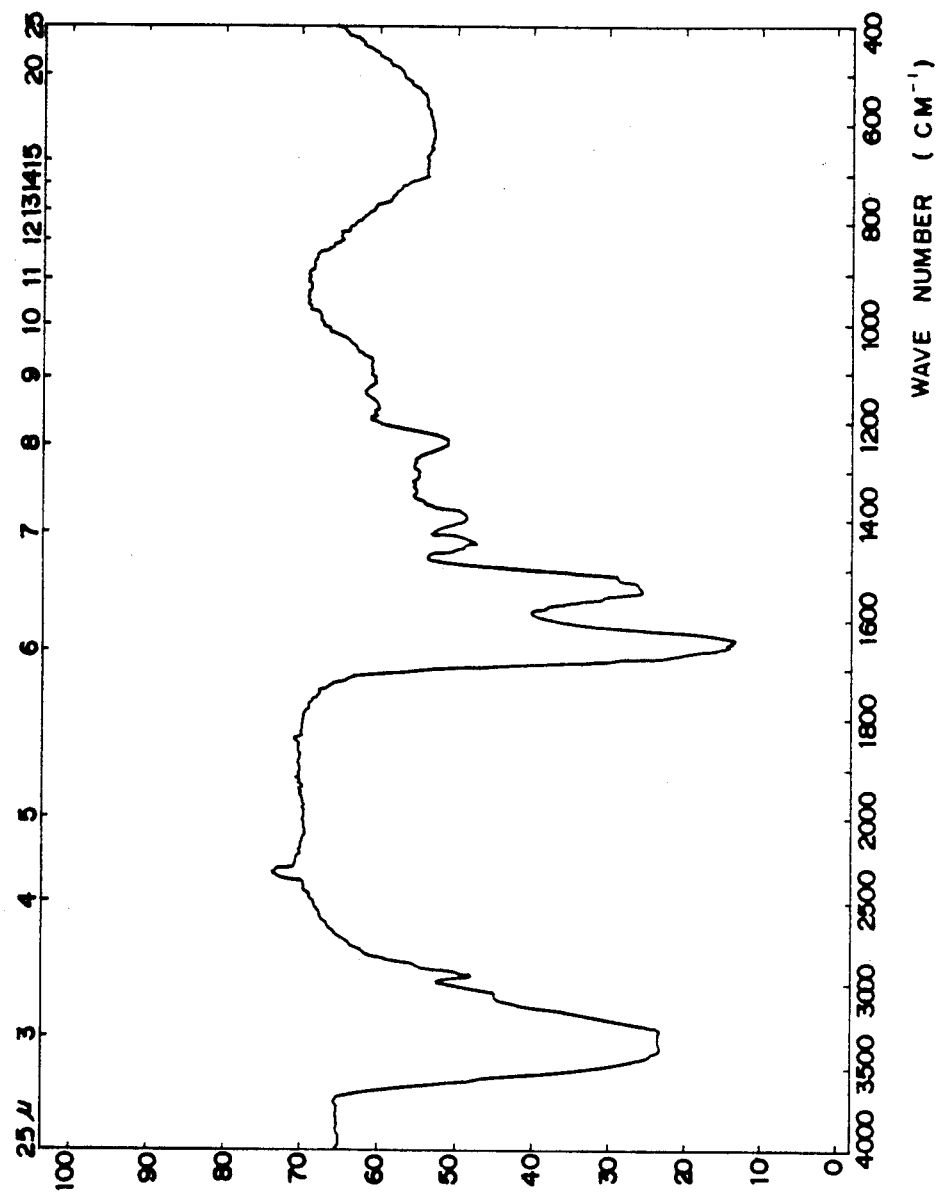
FIGS. 8 to 12, 14, 17 and 18 are infrared absorption spectra of the specimens obtained in Examples to 3, 5, 6 and 9 to 11 respectively.
Figure 9:
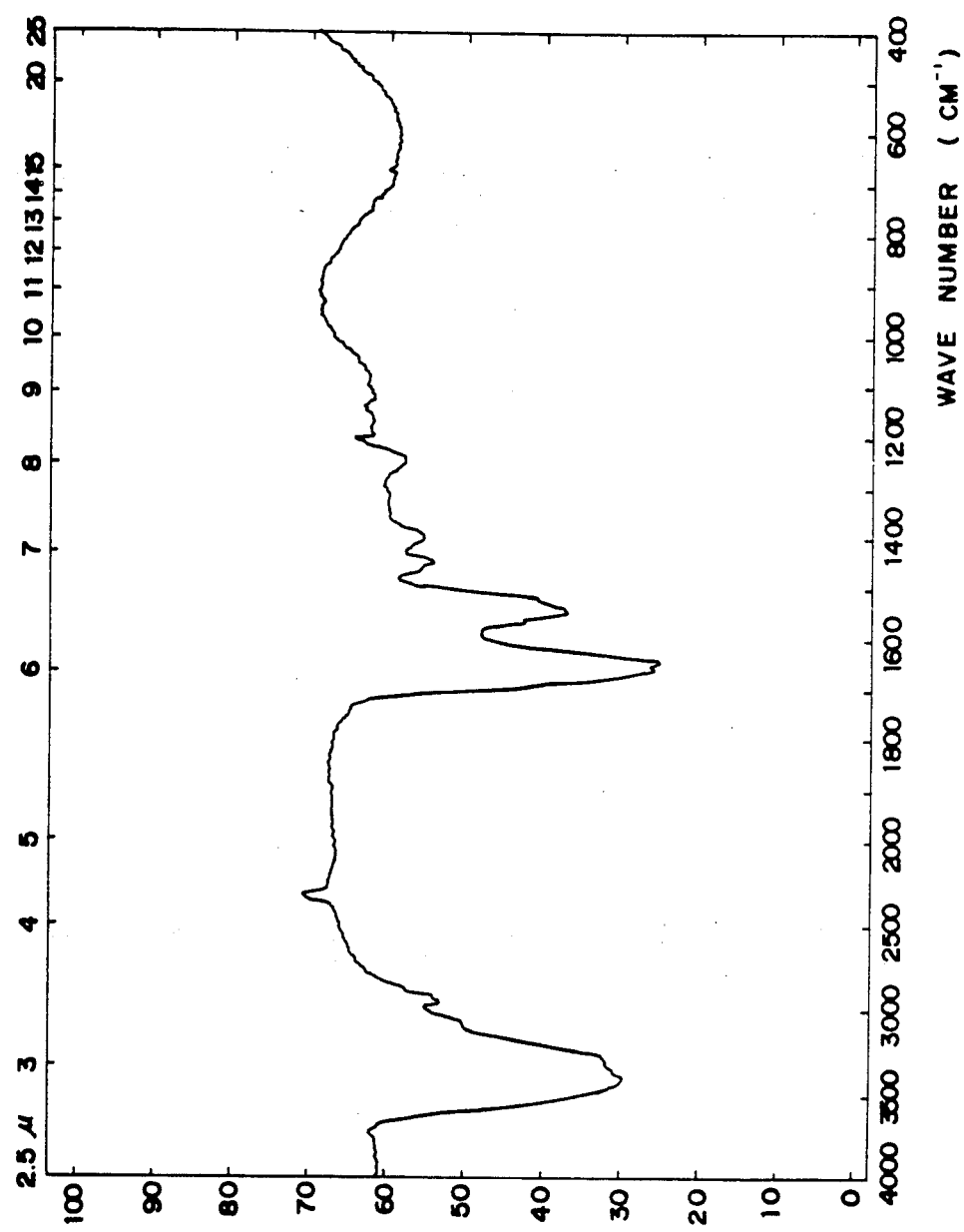
Figure 10:
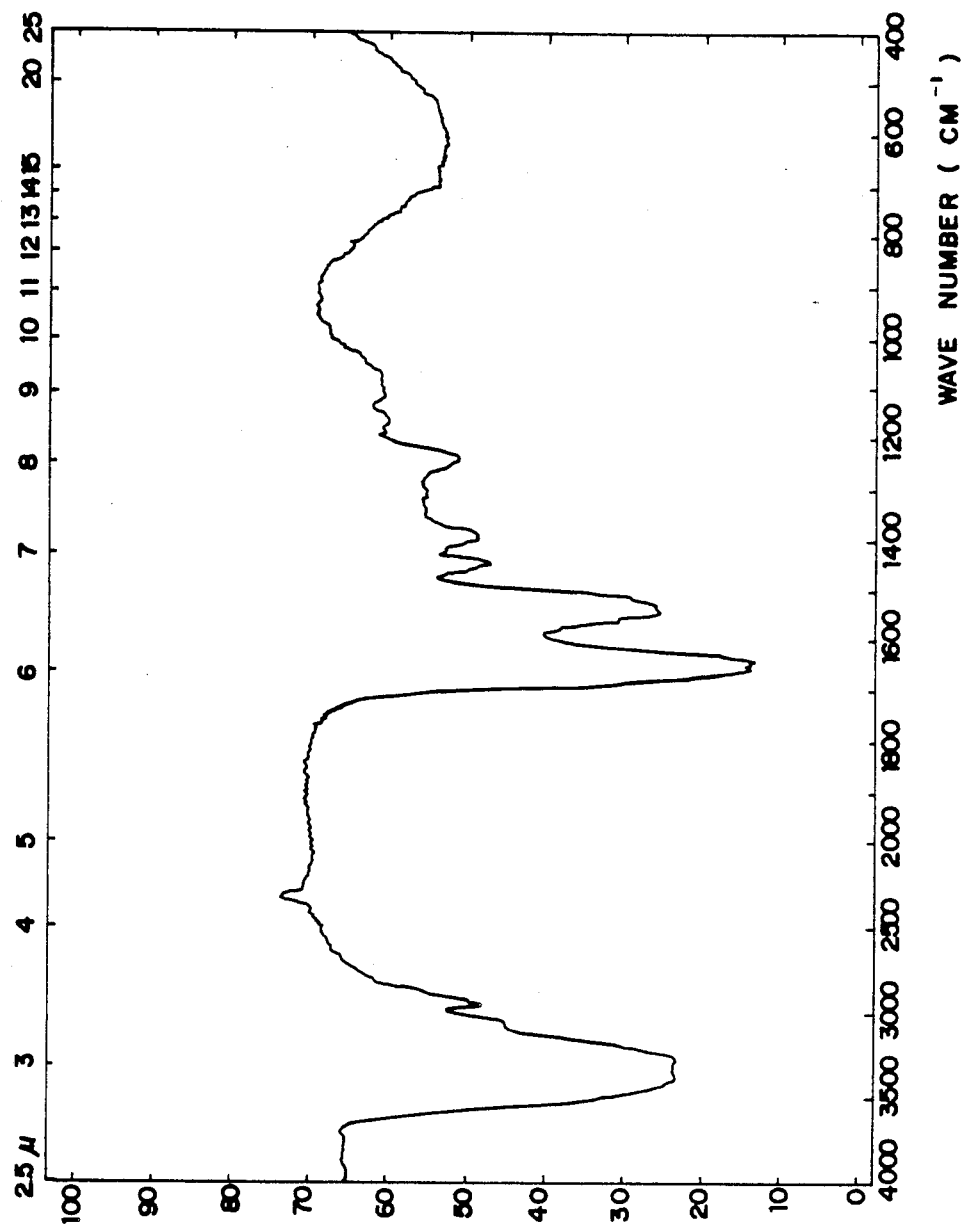
Figure 11:
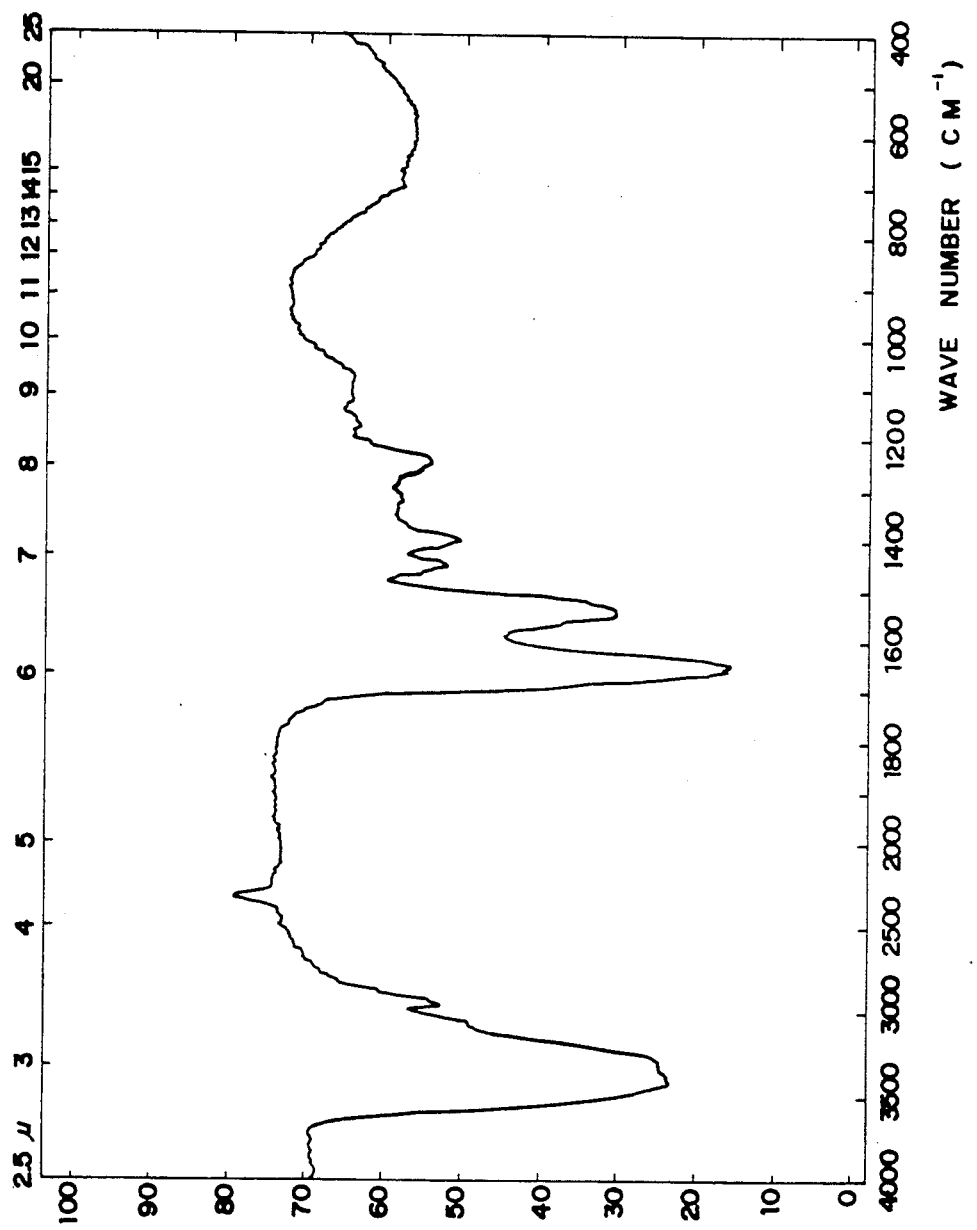
Figure 12:
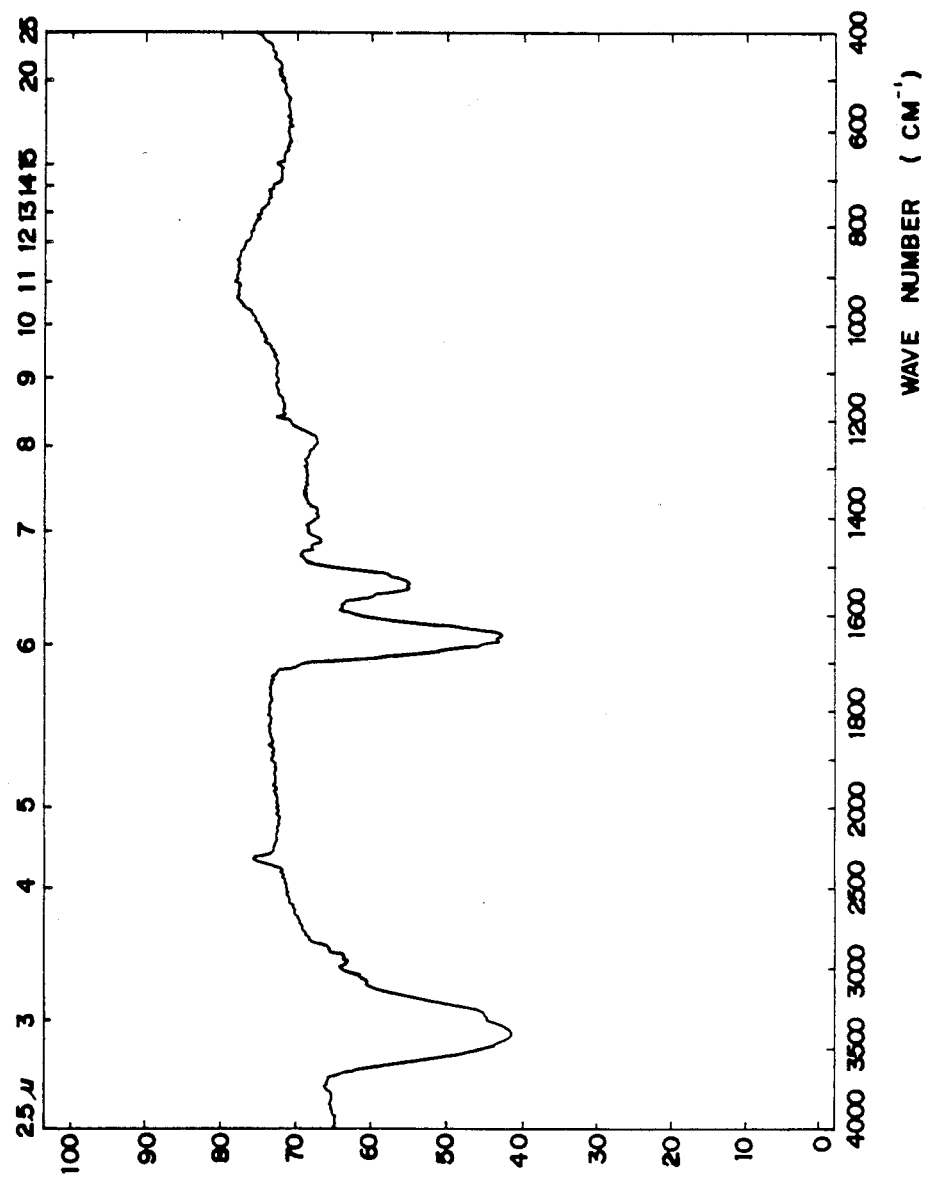
Figure 13:
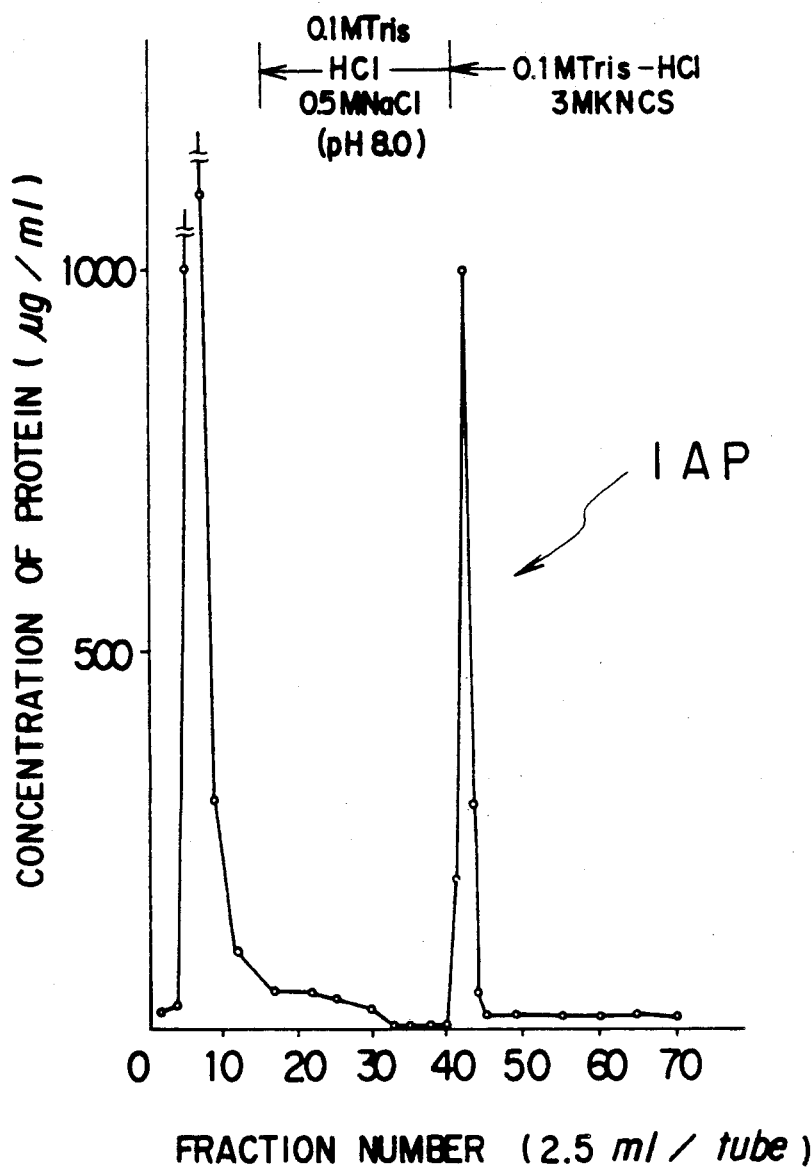
FIGS. 13, 15 and 16 are graphic representations of haptogrobin-sepharose column chromatography (Example 9), haptograbin-sepharose column chromatography (Example 10), and carboxymethylsepharose CL-6B column chromatography respectively.

Since the thus purified fraction still contained impurities even in an extremely minute amount, the fraction was condensed and dialysed against 0.01M phosphate buffer solution of pH 7.0 containing sodium chloride at 0.5 M, and then subjected to gel-filtration using a column (2.8 cm × 60 cm) of Biogel P-100 (made by Bio. Rad Co.), equilibrated by 0.01 M phosphate buffer solution of pH 7.0 containing sodium chloride at 0.5 M. The filtrate showed the identical pattern of proteins with that of IAP itself and had a peak in the molecular weight distribution at about 80,000 as measured by gel filtration (refer to FIG. 4).

Then, the filtrate was freeze-dried to obtain a non-deliquescent powdery white substance. The purity of this substance was determined by disc electrophoresis (set forth below.)

The final product (IAP) was subjected to disc electrophoresis using polyacrylamide gel of concentration of 7 5% as the supporting body and aqueous 1N potassium hydroxide-acetic acid buffer solution of pH 4.3 as the electrolyte solution under the conditions of 30 μg of specimen applied current of 4 mA, duration of 2 hours/gel, staining by Amido-black 10 B and destaining by aqueous 7% acetic acid solution to give an extremely sharp band at the distance of 2.221±0.061 cm from the end of spacer gel. The procedures were carried out the description by J. V. Maizel, Jr. (refer to "Biochem. Biophys. Res. Comm.", 13, 483(1963)).

FIG. 7 which illustrates the pattern of gel state and the pattern of electrophoresis of the specimen taken by a densitometer.

The rate of recovery of proteins, the rate of recovery of the physiological activity and the degree of purification of the product of each step of Example 1 are shown in Table 2, wherein the concentration of proteins was obtained by the method of Lowry et al (refer to J. Biol. Chem., 193, 265(1951)), while using bovine serum albumin as the standard, and the physiological activity was obtained by the method shown in detail in Example 12.

TABLE 2

| Step | Amount of solution (ml) | Concentration of protein (μg/ml) | Total amount of protein (mg) | Specific activity physiological (units/μg) | Yield of activity (%) | Degree of purication |
|---|---|---|---|---|---|---|
| Supernatant of culture medium | 10,000 | 2,000 | 22,000 | 0.318 | 100 | 1 |
| Eluate from hydroxyapatite column chromatography | 125 | 159 | 19.9 | 193.0 | 55 | 607 |
| Eluate from Carboxymethy Sepharose column chromatography | 45 | 251 | 11.3 | 321.0 | 52 | 1,009 |
| Eluate from Con A-Sepharose column chromatography | 50 | 176 | 8.8 | 380.0 | 48 | 1,195 |
| Filtrate by Biogel P-100 gel filtration | 40 | 168 | 6.7 | 429.0 | 41 | 1,349 |

The results are shown in FIG. 5 wherein the pattern of gel-state and the pattern of electrophoresis of the specimen taken by a densitometer are illustrated.

From these results, it has been confirmed that the final product (IAP) obtained in Example 1 was a pure substance of protein not substantially containing any impurities.

In order to see the subunit structure of the final product (IAP), it was subjected to the SDS (sodium dodecylsulfate)-polyacrylamide gel electrophoresis according to the method of A. L. Shapilo (refer to "Biochem. Biophys. Res. Comm.", 28, 815(1967)).

In an aqueous solution containing 1% of sodium dodecylsulfate, 1% of 2-mercaptoethanol and 4 M of urea, 50 micrograms (per one tube of gel) of the final product (IAP) was added, and after incubating the mixture for 2 hours at 37° C., it was applied onto a 10% polyacrylamide gel containing 1% of sodium dodecylsulfate, and after 4 hour-application per one tube of gel of a current of 8 mA, it was stained with Coomassie Blue and then destained with aqueous 7.5% acetic acid solution. The results are shown in FIG. 6 which illustrates the pattern of gel state and the pattern of electrophoresis of the specimen taken by a densitometer.

In a modified method, 50 μg of the final product (per one tube of gel, IAP) was added to an aqueous solution containing 1% of sodium dodecylsulfate and 1% of 2-mercaptoethanol and after incubation for 5 min. at 100° C., the mixture was applied onto a 12.5 % polyacrylamide gel and after 6.5 hour-application of 8 mA of current, it was treated with aqueous 20% trichloroacetic acid solution and then stained with aqueous 0.1% Coomassie Blue solution and then destained with aqueous 7.5% acetic acid solution. The results are shown in FIG. 7 which illustrates the pattern of gel state and the pattern of electrophoresis of the specimen taken by a densitometer.

The product obtained by the last step showed the isoelectric point of pH of 8.9. It contained about 95% by weight of protein as a major component, the amino acid-composition of the protein being shown in Table 3.

TABLE 3

| Composition of amino acid of IAP obtained in Example 1 Unit: μM/100 μM | | | |
|---|---|---|---|
| Amino acid | % | Amino acid | % |
| Aspartic acid | 7.5 | Methionine | 2.8 |
| Threonine | 7.3 | Isoleucine | 4.0 |
| Serine | 6.4 | Leucine | 7.8 |
| Glutamic acid | 10.0 | Tyrosine | 6.5 |
| Proline | 5.8 | Phenylalanine | 3.7 |
| Glycine | 8.8 | Lysine | 3.3 |
| Alanine | 9.3 | Histidine | 1.5 |
| Cystine/2 | 2.5 | Arginine | 6.4 |
| Valine | 6.5 | | |

EXAMPLE 2:

Lyophillized and preserved bacterial strain Tohama Phase I (the same as in Example 1), supplied by the same party as in Example 1 was cultured in the same manner as in Example 1. The supernatant of the culture medium obtained by separation of organisms therefrom was used as the starting material. The acetone which was cooled by dry ice was dropped on the 100 l of supernatant shaking under ice cooling to achieve the final concentration 60%. After that the precipitate was collected with a continuous centrifugal separator (5000 r.p.m., 4° C.)

After drying the thus obtained precipitate the thus obtained substance was dissolved in 500 ml of 0.01 M phosphate buffer solution of pH 6.0 and then was applied to a column (5 cm×4 cm) of hydroxypatite. The fractions containing IAP was eluted with 0.1 M phosphate buffer solution (pH 7.0) containing sodium chloride at 0.5 M. The eluted fractions was condensed and dialyzed against 0.01 M phosphate buffer solution of pH 6.0, and then applied to a column (2.5 cm×25 cm) of CM-Sepharose CL-6B which had been equilibrated with the buffer and the active substance was eluted with 0.1 M phosphate buffer solution containing sodium chloride at 0.5 M. Further the thus eluted fractions was collected, condensed and dialyzed against 0.1 M phosphate buffer solution (pH 7.0) containing sodium chloride at 0.5 M. After that, the fractions was applied to a column (2 cm×105 cm) of Biogel P-150 which had been equilibrated with 0.1 M phosphate buffer solution containing 0 5 M sodium chloride and 4 M urea. The filtrate which showed a peak the molecular weight of approximate 80,000 as measured by gel filtration was freeze-dried and thus obtained 38 mg of powdery product white in colour. It is composed chemically of 97% by weight of protein and 1 to 2% by weight of glycoside, no lipid being detected.

EXAMPLE 3:

Lyophillized and preserved bacterial strain Tohama Phase I (the same as in Example 1), supplied by the same party as in Example 1, was cultured in the same manner as in Example 1, and 100 liters of the supernatant was obtained from the culture medium.

An aqueous 50% zinc chloride solution was added to the supernatant until the concentration of zinc chlorine in the mixture became 1% while shaking the supernatant at room temperature, the final pH of the mixture being 6.0. The thus separated precipitate was collected by filtration and dissolved in aqueous 10% disodium hydrogen phosphate solution. This solution was next applied to a column (10 cm×5 cm) of hydroxyapatite and was washed with 0.1 M phosphate buffer solution at pH 7.0 and then was eluted with 0.1 M phosphate buffer solution containing 0.5 M sodium chloride. The obtained eluate was condensed and was applied to column chromatography of a column (2.5 cm×100 cm) of Sephacryl S-200 (made by Pharmacia Fine Chemicals Inc.) and the column was eluted by aqueous 0.1 M phosphate buffer solution containing sodium chloride at 0.5 M. The eluate was then subjected to gel filtration using a column (2.8 cm×60 cm) of Biogel P-100, equilibrated with 0.01 M Phosphate buffer solution of pH 7.0 containing sodium chloride at 0.5 M. By freeze-drying the filtrate, powdery product white in colour was obtained. The molecular weight of the product was approximately 72,000 as measured by gel filtration. It was composed by about 96% by weight of protein and 1 to 2% by weight of glycoside, no lipid being detected.

The product obtained by the last step gave a single band in disc electrophoresis with a gel of pH 4.3 and showed the isoelectric point of pH of 8.8. The amino acid-composition of the protein was shown in Table 4.

TABLE 4

Composition of amino acid of IAP obtained in Example 3
Unit: $\mu M/100 \mu M$

| Amino acid | % | Amino acid | % |
|---|---|---|---|
| Aspartic acid | 7.8 | Methionine | 2.7 |
| Threonine | 7.6 | Isoleucine | 3.6 |
| Serine | 6.9 | Leucine | 7.6 |
| Glutamic acid | 8.8 | Tyrosine | 6.6 |
| Proline | 5.9 | Phenylalanine | 3.7 |

TABLE 4-continued

Composition of amino acid of IAP obtained in Example 3
Unit: $\mu M/100 \mu M$

| Amino acid | % | Amino acid | % |
|---|---|---|---|
| Glycine | 9.3 | Lysine | 4.2 |
| Alanine | 9.2 | Histidine | 1.0 |
| Cystine/2 | 2.1 | Arginine | 6.2 |
| Valine | 6.8 | | |

EXAMPLE 4:

The same lyophillized and preserved bacterial strain of *Bordetella pertussis* as in Example 1 (supplied by the same party in Example 1) was cultured in Bordet-Gengou culture medium at 37° C. for 2 days and further in Bordet-Gengou slant culture medium at 37° C. for 20 to 24 hours, and a platinum loopful of the bacteria was inoculated into the modified Cohen-Wheeler solid culture medium (hereinafter referred to as CA medium) added with charcoal having the composition shown in Table 5 and cultured for 48 hours at 37° C. Five kilograms of wet bacterial cells thus obtained were suspended into 5 litres of distilled water and retained at 56° C. for 1 hour.

After cooling the suspension to room temperature, sodium ethylmercurithiosalicylate(thimerosal) was added to the suspension in an amount to make the concentration of thimerosal in the suspension 0.01%, and the suspension was subjected to centrifugation at 15,000 r.p.m. for 30 min to collect the cells. The collected cells were suspended in distilled water containing 4 M urea and 1 M sodium chloride, and the suspension was subjected to ultrasonic waves at 4° C. to destory the bacterial cells.

The thus treated suspension was subjected to centrifugation at 15,000 r.p.m. for 30 min. and the precipitate-free supernatant was dialyzed against water. After being equilibrated with aqueous 0.1 M phosphate buffer of pH 0.6, the dialyzate was applied onto a column (10 cm×5 cm) of hydroxya-patite. After washing the column with 0.01 M phosphate buffer solution of pH 6.0 and again washing the column with 0.1 M phosphate buffer solution of pH 7.0, a fraction was obtained by eluting with 0.1 M phosphate buffer solution containing sodium chloride at 0.5 M at pH 7.0.

The fraction was equilibrated with 0.01 M phosphate buffer solution of pH 6.0, and then applied onto a column (2.5 cm×30 cm) of Carboxymethyl-Sepharose CL-6B. The column was at first washed with 0.05 M phosphate buffer solution of pH 6.0 and then eluted with 0.1 M phosphate buffer solution of pH 7.0 containing sodium chloride at 0.5 M to collect the eluate. The eluate was condensed and dissolved in 0.1 M phosphate buffer solution of pH 7.1 containing 4 M urea and 0.5 M sodium chloride. Then the solution was applied to a column (2.5 cm×115 cm) of Sephacryl S-200. The eluate from the column was freeze-dried to give an active substance of molecular weight of 74,000 as measured by gel filtration and of the composition of more than 95% by weight of protein and 2% by weight of glucide, no lipid being detected.

TABLE 5

| Composition of CA medium | |
|---|---|
| Casamino acid | 10 g |
| Yeast extract | 1 g |
| Potassium dihydrogen phosphate | 0.5 g |
| Soluble starch | 1.5 g |

TABLE 5-continued

| Composition of CA medium | |
| --- | --- |
| Aqueous 0.5% cupric sulfate solution | 1 ml |
| Aqueous 1% magnesium chloride solution | 1 ml |
| Polypeptone | 5 g |
| Aqueous 1% cystine solution | 2.5 ml |
| Aqueous 0.5% ferric sulfate solution | 1 ml |
| Sodium chloride | 2.0 g |
| Powdery agar—agar | 18 g |
| Distilled water | 1,000 ml |

(Note) In use, the pH of this medium is adjusted to 7.2, and 5 g of powdery charcoal is added to the medium, and then the whole mixture was autoclaved for 20 min at 121° C.

The product obtained by the last step gave a single band in disc electrophoresis with a gel of pH 4.3 and showed the isoelectric point of pH of 8.5. The amino acid-composition of the protein was shown in Table 6.

TABLE 6

Composition of amino acid of IAP obtained in Example 4
Unit μM/100 μM

| Amino acid | % | Amino acid | % |
| --- | --- | --- | --- |
| Aspartic acid | 7.5 | Methionine | 2.6 |
| Threonine | 6.9 | Isoleucine | 4.6 |
| Serine | 6.3 | Leucine | 7.7 |
| Glutamic acid | 9.9 | Tyrosine | 6.5 |
| Proline | 5.5 | Phenylalanine | 4.0 |
| Glycine | 9.1 | Lysine | 3.9 |
| Alanine | 10.7 | Histidine | 0.9 |
| Cystine/2 | 1.8 | Arginine | 6.1 |
| Valine | 6.6 | | | showing the activity, was condensed and dialysed two times using a membrane of the maximum permeated molecular weight of 8,000 (Catalogue No. 3787-F25, made by Thomas Inc.) for total period of 12 hours against distilled water, and the dialyzate was further dialyzed two times using the same membrane against aqueous 0.01 M phosphate buffer solution of pH 6.0 for total period of 12 hours. Subsequently, the dialyzate was applied onto a column (1.5 cm × 10 cm) of Carboxymethyl-Sepharose CL-6B equilibrated with 0.01 M phosphate buffer solution of pH 6.0 No activity was detected in the liquid which passed through the column. Then, the column was eluted with aqueous 0.1 M phosphate buffer solution of pH 7.0 containing sodium chloride at 0.5 M. Although the activity of promoting the secretion of insulin was detected in the eluate, a minute amount of impurities was detected in the eluate by disc electrophoresis, and accordingly, after condensing the eluate, the condensate was subjected to gel-filtration using a column of Sephacryl S-200.

The filtrate showed the identical pattern of proteins with that of IAP itself and had a peak in the molecular weight distribution at about 77,000 as measured by gel filtration. By freeze-drying the filtrate, a highly purified substance was obtained as the product. The rate of recovery of the activity, the degree of purification, etc. in the process of purification are shown in Table 7 The purity of the product was determined by the method of disc electrophoresis according to J. V. Maizel, Jr. (refer to Biochem. Biophys. Res. Comm., 13, 483 (1963) and Example 1).

TABLE 7

| Specimen | Amount of solution (ml) | Concentration of protein (μg/ml) | Total amount of protein (mg) | Specific activity (units/μg) | Yield of activity (%) | Degree of purification |
| --- | --- | --- | --- | --- | --- | --- |
| Supernatant of culture medium | 10,000 | 2,300 | 23,000 | 0.84 | 100 | 1 |
| Filtrate after Gel-filtration | 43 | 158 | 6.8 | 1342 | 47 | 1598 |

Note:
Concentration of protein in the specimen was determined by the method of Lowry (refer to J. Biol. Chem., 193, 265(1951))

EXAMPLE 5:

Lyophillized and preserved bacterial strain Maeno Phase I (supplied by the same party as in Example 1) was cultured in the same manner as in Example 1 and a supernatant was prepared from the culture medium also in the same manner as in Example 1.

After adjusting the pH of 10 liters of the supernatant to 6.0 with the addition of aqueous 1 N hydrochloric acid solution, the supernatant was poured into a hydroxyapatite column (2.5 cm × 4 cm) at a rate of 200 ml/hour as the first step. Almost all protein was passed through the column without being adsorbed, and the activity of promoting insulin-secretion was scarcely observed in the liquid which passed through the column.

Although the column was washed with aqueous 0.01 M phosphate buffer solution of pH 6.0 and then washed again with aqueous 0.1 M phosphate buffer solution of pH 7.0 to elute protein adsorbed on the column, the activity of promoting the secretion of insulin was not detected in the eluate. Then, the column was washed again with aqueous 0.1 M phosphate buffer solution of pH 7.0 containing sodium chloride at 0.5 M. The eluate, The product obtained by the last step gave a single band in disc electrophoresis with a gel of pH of 4.3 and showed the isoelectric point of pH of 9.2. It contained about 98% by weight of protein as a major component, the amino acid-composition of the protein being shown in Table 8.

TABLE 8

Composition of amino acid of IAP obtained in Example 5
Unit: μM/100 μM

| Amino acid | % | Amino acid | % |
| --- | --- | --- | --- |
| Aspartic acid | 7.7 | Methionine | 2.5 |
| Threonine | 7.0 | Isoleucine | 3.8 |
| Serine | 6.8 | Leucine | 8.1 |
| Glutamic acid | 9.4 | Tyrosine | 5.8 |
| Proline | 6.4 | Phenylalanine | 4.1 |
| Glycine | 9.6 | Lysine | 3.1 |
| Alanine | 9.1 | Histidine | 1.3 |
| Cystine/2 | 1.7 | Arginine | 6.4 |
| Valine | 7.1 | | |

EXAMPLE 6:

Lyophillized and preserved bacterial strain Tohama Phase I of *Bordetella pertussis* (supplied by the same party as in Example 1) was cultured in the same manner as in Example 1 and 10 liters of supernatant of the cultured liquid was obtained by the same procedures as in Example 5 as the starting material for preparing the object product of the present invention, the procedures for preparing the object product having been carried out in quite the same procedures as in Example 5. Namely, the difference between Examples 5 and 6 is only the difference between strains of the same bacterial species. The filtrate showed a single peak corresponding to molecular weight of 68,000 as measured by gel filtration.

The specific activity, the yield of activity and the degree of purification of the final product are shown in Table 9 as compared to those of the starting material, supernatant.

The composition of amino acid constituting the product determined after hydrolyzing the product in aqueous 6N hydrochloric acid at 110° C. for 16 hours by the method of Lowry, O. H. et al. (loc. cit.) is shown in Table 10.

TABLE 9

| Specimen | Amount of solution (ml) | Concentration of protein (μg/ml) | Total amount of protein (mg) | Specific activity (units/μg) | Yield of activity (%) | Degree of purification |
|---|---|---|---|---|---|---|
| Supernatant of culture medium | 10,000 | 3,500 | 35,000 | 0.56 | 100 | 1 |
| Filtrate after Gel-filtration | 65 | 112.3 | 7.3 | 1,349.0 | 50.2 | 2,408.9 |

Note:
Concentration of protein in the specimen was determined by the method of Lowry (refer to J. Biol. Chem., 193, 265(1951))

The thus obtained product gave a single band in disc electrophoresis with a gel of pH 4.3 and showed the isoelectric point of pH of 9.3. It contained about 98% by weight of protein as a major component, the amino acid-composition of the protein being shown in Table 10.

TABLE 10

Composition of amino acid of IAP obtained in Example 6
Unit: μM/100 μM

| Amino acid | % | Amino acid | % |
|---|---|---|---|
| Aspartic acid | 7.6 | Methionine | 2.7 |
| Threonine | 7.6 | Isoleucine | 3.8 |
| Serine | 6.9 | Leucine | 8.2 |
| Glutamic acid | 8.9 | Tyrosine | 6.1 |
| Proline | 5.6 | Phenylalanine | 4.1 |
| Glycine | 9.3 | Lysine | 3.8 |
| Alanine | 9.9 | Histidine | 1.1 |
| Cystine/2 | 1.4 | Arginine | 6.3 |
| Valine | 7.1 | | |

EXAMPLE 7:

The same lyophillized and preserved strain Tohama Phase I of *Bordetella pertussis* as in Example 1 (supplied by the same party as in Example 1) was cultured in the same manner as in Example 1. Ten liters of the supernatant of the culture medium was applied onto a column (5 cm×2 cm) of hydroxyapatite at a flow rate of 60 ml/hour. After washing the column with 300 ml of 0.01 M phosphate buffer solution of pH 7.0, the column was eluted by 0.1 M phosphate buffer solution of pH 7.0 containing sodium chloride at 0.5 M, at a flow rate of 15 ml/hour. The eluate was condensed to about 15 ml in the presence of Ficol 400 (made by Pharmacia Fine Chemicals Inc.), and then dialysed 4 times for total period of 24 hours against 4 liters of distilled water and then further dialysed 4 times for total period of 24 hours against 1 liter of 0.01 M acetate buffer solution of pH 4.5 containing sodium chloride at 0.1 M or lithium chloride sodium chloride at 0.1 M. The final dialyzate was applied onto a column 1.2 cm×8 cm of p-Acetoxymercurianiline-Sepharose 6MB (see Note), the column having been equilibrated with the same buffer solution as mentioned above, at a flow rate of 5 ml/hour, and after washing the column well with the same buffer solution, the adsorbed substances on the column was eluted with the same buffer solution containing L-cystein at 0.01 M. The eluate was condensed in the presence of Ficol-400, and the condensate was dialysed 3 times for total period of 12 hours against 2 liters of 0.1 M phosphate buffer solution of pH 7.0 containing urea and sodium chloride, respectively at 4 M and 0.5 M. The dialyzate was subjected to gel-filtration using a column (2.8cm×95 cm)of Sephacryl S-200. The filtrate showed a single peak corresponding to molecular weight of 65,000 as measured by gel filtration the peak corresponding to the peak of the activity of promoting the secretion of insulin. The filtrate was dialysed 5 times for the total period of 48 hours against distilled water and consequently freeze-dried to yield 2.1 mg of white powder. The thus obtained product showed a single band on polyacrylamide gel-electrophoresis (pH of the gel being 4.3) and a composition of more than 98% by weight of protein. Neither carbohydrate nor lipid was detected therein.

The product obtained by the last step gave a single band in disc electrophoresis with a gel of pH 4.3 and showed the isoelectric point of pH of 8.7. The amino acid-composition of the protein was shown in Table 11.

TABLE 11

Composition of amino acid of IAP obtained in Example 7
Unit: μM/100 μM

| Amino acid | % | Amino acid | % |
|---|---|---|---|
| Aspartic acid | 7.5 | Methionine | 3.3 |
| Threonine | 7.2 | Isoleucine | 3.8 |
| Serine | 5.9 | Leucine | 8.0 |
| Glutamic acid | 9.8 | Tyrosine | 5.1 |
| Proline | 5.9 | Phenylalanine | 3.9 |
| Glycine | 9.4 | Lysine | 3.3 |
| Alanine | 10.0 | Histidine | 1.2 |
| Cystine/2 | 2.2 | Arginine | 6.1 |
| Valine | 7.6 | | |

Note: Preparation of p-acetoxymercurianiline-Sepharose 6MB

Four grams of CNBr-activated Sepharose 6MB (made by Pharmacia Fine Chemicals Inc.) is repeatedly washed and swollen on a glass filter by using 1 liter of aqueous solution of hydogon chloride of $10^{-3}$N. A separately prepared solution obtained by dissolving 172 mg (0.5 mol) of p-acetoxymercurianiline in 50 ml of a 0.1 M sodium hydrogen carbonate buffer solution containing 60% of dimethylformamide and 0.5 M of sodium chloride of pH 8.3 is added to the swollen Sepharose, and the mixture is well shaken at room temperature of 22° to 25° C. for 2 hours. Then, the reaction product is washed well with the above-mentioned buffer solution and after adding 50 ml of aqueous 1 M monoethanolamine solution of pH 9.0 to the product, the gel-like mixture is well shaken at room temperature for 2 hours. The thus formed gel is suction filtered on a glass filter, washed several times alternately with 1 liter of 0.1 M borate buffer solution of pH 8.5 and 1 liter of 0.1 M acetate buffer solution of pH 4.0 and finally equilibrated with 0.01 M acetate buffer solution of pH 4.5 containing sodium chloride at 0.1 M and finally equilibrated with 0.01 M acetate buffer of pH 4.5 containing sodium chloride at 0.1 M. Otherwise the gel is previously treated with the same buffer solution as above containing 1% of 2-mercaptoethanol and then sufficiently washed and equilibrated with the same buffer solution shown above.

EXAMPLE 8:

The same lyophillized and preserved strain of *Bordetella pertussis* as in Example 1, (supplied by the same party as in Example (1) was cultured in the same manner as in Example 1 to obtain the supernatant.

Ten liters of the supernatant of the culture medium was applied onto a column (5 cm × 2 cm) of hydroxyapatite at a flow rate of 60 ml/hour. After washing the column with 300 ml of 0.01 M phosphate buffer solution of pH 7.0, the column was again washed with 0.1 M phosphate buffer solution of pH 7.0 at a rate of 15 ml/hour. The eluate was condensed to about 15 ml in the presence of Ficol 400 (made by Pharmacia Fine Chemicals Inc.), and the condensate was dialysed 4 times for the total period of 24 hours against 1 liter of 0.01 M phosphate buffer solution of pH 7.0. The dialyzate was applied onto a column (1.8 cm×13 cm) of anti-IAP antibody-Sepharose 4B (refer to Note below). Then, the column was washed well with about 200 ml of 0.01 M phosphate buffer solution of pH 7.0 containing sodium chloride at 0.1 M and eluted with an aqueous solution of 0.1 M of glycin-hydrochloride, 2mM of ethylendiamintetraacetic acid and 0.15 M of sodium chloride and of pH 3.0 at a flow rate of 60 ml/hour. The eluate was neutralized at once with aqueous 1M glycine buffer solution of pH 11.5 and then dialysed 3 times for the total period of 48 hours against distilled water. Upon freeze-drying the dialyzate, 1.9 mg of white powder was obtained as the product of molecular weight of 70,000±5,000 as measured by gel filtration method. The product showed a single band on polyacrylamide gel electrophoresis (pH of the gel being 4.3) and had the composition of about 97% or more of protein and less than 1% of glucide, no lipid having been detected.

The product obtained by the last step gave a single band in disc electrophoresis with a gel of pH of 4.3 and showed the isoelectric point of pH of 9.4. The amino acid-composition of the protein was shown in Table 12.

TABLE 12

Composition of amino acid of IAP obtained in Example 8
Unit: μM/100 μM

| Amino acid | % | Amino acid | % |
|---|---|---|---|
| Aspartic acid | 7.9 | Methionine | 3.0 |
| Threonine | 6.8 | Isoleucine | 3.8 |
| Serine | 7.6 | Leucine | 7.5 |
| Glutamic acid | 10.0 | Tyrosine | 5.6 |
| Proline | 6.2 | Phenylalanine | 3.8 |
| Glycine | 8.7 | Lysine | 3.2 |
| Alanine | 9.1 | Histidine | 1.1 |
| Cystine/2 | 2.0 | Arginine | 6.6 |
| Valine | 7.0 | | |

Note: Preparation of Anti-IAP antibody-Sepharose 4B

Ten grams of CNBr-activated Sepharose 4B (made by Pharmacia Fine Chemicals Inc.) is washed and swollen on a glass filter by using 2 liters of aqueous $10^{-3}$N hydrogen chloride solution.

A separately prepared solution obtained by dissolving 100 g of anti-IAP antibody in 50 ml of aqueous 0.1 M sodium hydrogen carbonate buffer solution of pH 8.3 containing sodium chloride of 0.5 M is added to the swollen Sepharose, and the mixture is shaken well at room temperature (22° to 25° C.) for 2 hours. Then the reaction mixture is filtered with a glass filter and the residue was washed several times with the same buffer solution to remove excessive anti-IAP antibody After adding 100 ml of aqueous 1 M monoethanolamine solution, the mixture is shaken well for 2 hours at room temperature. Then, the mixture is washed several times with the above-mentioned buffer solution and then 3 times with 1 liter of 0.1 M acetate buffer solution of pH 4.0 containing sodium chloride at 0.5 M.

Finally, the mixture was again washed with the above-mentioned buffer solution and preserved for use at 4° to 8° C.

Some data on the physical properties of the products obtained in each of Examples are shown in the following table:

TABLE 13

| Specimen (Number of Example) | Isoelectric point[1] | Specific rotation[2] | Absorption of ultraviolet[3] | Sedimentation constant[4] | Nuclear magnetic resonance spectrum[5] | Absorption of infrared[6] | Elementary Analysis[7] (%) | | | |
|---|---|---|---|---|---|---|---|---|---|---|
| | | | | | | | C | H | N | S |
| 1 | 8.9 | −27° | λmax 279 nm (log ε 4.70) | 6.4 | 1.2~3.3 ppm<br>4.0~6.0 ppm<br>6.7~8.8 ppm | FIG. 8 | 46.6 | 6.7 | 14.4 | 1.7 |
| 2 | 9.0 | −28° | λmax 278 nm (log ε 4.71) | 6.3 | 1.5~3.2 ppm<br>4.3~5.9 ppm<br>6.7~8.6 ppm | FIG. 9 | 50.5 | 7.3 | 13.2 | 1.4 |
| 3 | 8.8 | −26° | λmax 277 nm (log ε 4.82) | 6.2 | 1.2~3.1 ppm<br>4.1~5.8 ppm<br>6.8~8.7 ppm | FIG. 10 | 47.8 | 6.9 | 14.8 | 1.5 |
| 4 | 8.5 | −32° | λmax 277 nm (log ε 5.03) | 6.5 | 1.3~3.4 ppm<br>4.0~5.9 ppm<br>6.8~8.8 ppm | — | 49.5 | 7.4 | 15.3 | 1.3 |
| 5 | 9.2 | −29° | λmax 276 nm (log ε 4.79) | 6.6 | 1.4~3.1 ppm<br>4.2~6.0 ppm<br>6.9~8.5 ppm | FIG. 11 | 46.8 | 6.9 | 14.4 | 1.7 |
| 6 | 9.3 | −29° | λmax 276 nm | 6.6 | 1.3~3.5 ppm | FIG. 12 | 46.6 | 6.7 | 14.8 | 1.6 |

TABLE 13-continued

| | | | | | | | | | | |
|---|---|---|---|---|---|---|---|---|---|---|
| | | | (log ε 4.92) | | 4.3~5.8 ppm | | | | | |
| | | | | | 6.7~8.7 ppm | | | | | |
| 7 | 8.7 | −28° | λmax 274 nm | 6.8 | 1.2~3.1 ppm | — | 52.0 | 7.4 | 15.1 | 1.3 |
| | | | (log ε 5.01) | | 4.1~5.9 ppm | | | | | |
| | | | | | 6.8~8.5 ppm | | | | | |
| 8 | 9.4 | −30° | λmax 275 nm | 6.7 | 1.3~3.5 ppm | — | 51.3 | 7.0 | 15.4 | 1.5 |
| | | | (log ε 4.87) | | 4.0~6.0 ppm | | | | | |
| | | | | | 6.9~8.7 ppm | | | | | |

Notes in the table are as follows:

[1] Determined following the method described in
Wringley, C. W., "J. Chromatogr., 36, 362–372(1968)",
under the following conditions:
(a) Composition of the tube for determination is as follows:
Gel layer: 4% by weight of polyacrylamide and 2.89% by weight of pharmalyte.
Specimen layer: 10 μg of specimen, 30% by weight of glycerol and 2% by weight of pharmalyte.
Protecting layer: 8 mg of glutamic acid, 30% by weight of glycerol and 2% by weight of pharmalyte.
(b) In anode side, aqueous 0.02M phosphoric acid solution, and in cathode side aqueous 0.1M sodium hydroxide solution were respectively placed, and applied a constant voltage of 200 V at 4° C. to pass an electric current for 5 hours.
(c) After 5 hours, the gel layer was collected and cut into 0.5 cm in thickness, and 1 ml of distilled water was added to the thus obtained cutting. After leaving the cuttings for one day, the pH of the extract of the cutting was detected at 4° C.
[2] The specimen was dissolved into aqueous 0.1M phosphate buffer solution containing 2M of urea to be a concentration of 1.95 mg/ml. The solution was applied to the polarimeter of sodium D-line at 25° C. on determination of the specific rotation.
[3] The specimen was dissolved in distilled water at a concentration of 40 to 50 μg/ml of pH of 6.3.
[4] The specimen was dissolved in aqueous 0.1M potassium dihydrogen phosphate containing 2M of urea, at pH of 4.79 and at a concentration of 300 to 400 μg/ml. Determination was carried out at 15° C. under the rotation of 60,000 r.p.m.
[5] The specimen was dissolved in heavy water at a concentration of 10 mg/ml, and determination was carried out at room temperature.
[6] One mg of the specimen was mixed well with 100 mg of crystalline potassium bromide, and after shaping a form of tablet, it was determined.
[7] The specium (15~20 mg) was dialyzed against distilled water for 4 to 5 days at 4° C. and then lyophillized. The obtained powder was dried at 55° C. for 24 hrs in vacuum.

EXAMPLE 9:

The lyophillized and preserved bacterial strain Tohama Phase I of *Bordetella pertussis* as in Example 1 (supplied by the same party in Example 1) was cultured in the same manner as in Example 1, and the supernatant obtained by the same manner as in Example 1 was used as the starting material for purely isolating the substance having insulin secretion promoting action as follows.

After adjusting the pH of the supernatant to 6.0 with 1N hydrochloric acid, 10 liters of the supernatant was poured into a hydroxyapatite column (2.5 cm × 4 cm) at a flow rate of 200 ml/hour. In this case, almost all the proteins passed through the column without being adsorbed onto the column, and the present substance having insulin secretion promoting activity was scarcely detected in the eluate.

For the elution of the thus adsorbed substance the column was first washed with a 0.01 M phosphate buffer solution of pH 6.0 and then with a 0.1 M phosphate buffer solution of pH 7.0, however, the present substance having insulin secretion promoting action was not eluted by such a treatment and it was eluted by washing the column with 0.1 M phosphate buffer solution additionally containing 0.5 M sodium chloride and of pH 7.0.

The thus obtained eluate was condensed and after introducing the condensate into a dialyzer having a dialyzing membrane with a maximum molecular weight of 8,000 (Cat. Number 3787-F-25, made by Thomas Company), the eluate was dialyzed two times against distilled water for total 12 hours and further two times against 0.01 M phosphate buffer solution for total 12 hours. The thus dialyzed solution containing the active substance was condensed, and the condensate was passed through a haptoglobin-sepharose column (5 cm × 20 cm). No activity was detected on the substances which were not adsorbed on this column.

Then, after throughly washing the column with 0.1 M tris-hydrochloric acid buffer solution containing 0 5 M sodium chloride of pH 8.0, the adsorbed substances on the column was eluated by passing a 0.1 M tris-hydrochloric acid buffer solution containing 3 M KNCS of pH 10.0 (refer to FIG. 13). The thus obtained eluate was dialyzed in a dialyzer having a dialyzing membrane with a maximum molecular weight of 3500 (Cat. number of VT-371 made by Hani Chemical Company) against a 0.1 M phosphate buffer solution additionally containing 2 M urea of pH 7.0 to obtain a dialyzate containing purified substance having insulin secretion promoting activity.

Table 14 shows the amount, the total amount of protein, the specific activity and the rate of purification of respective solutions after respective steps mentioned above as follows.

TABLE 14

| Step | Amount (ml) | Total amount of solution (mg) | Specific activity (units/μg) | Rate of purification |
|---|---|---|---|---|
| Supernatant | 10,000 | 22,000 | 0.318 | 1 |
| After treating with a hydroxyapatite column | 125 | 19.9 | 193 | 607 |
| After treating with haptoglobin-sepharose column | 2.6 | 2.6 | 1480 | 4654 |

The thus obtained substance having insulin secretion promoting action showed the following physical properties (1) to (10).

(1) Molecular weight:

(i) The molecular weight of the present product was approximately 68,000 as measured by gel filtration.

(ii) Molecular weight of the thus obtained active substance determined by the ultra-centrifuge for analysis ("Hitachi ultracentrifuge Model UCA-1 for analysis", made by Hitachi Works, Ltd.) on a solution in 0.01 M potassium dihydrogen phosphate buffer solution additionally containing 0.1 M sodium chloride and 2 M urea at 15° C. under 60,000 r.p.m. was 111,625±2,124 with the constant of sedimentation equilibrium of 6.6S.

(2) Content of protein:

The content of protein in the substance measured by the method of Lowry was not less than 98%.

(3) Composition of amino acids:

The composition of amino acids of the substance obtained after hydrolyzing for 24 hours in 6 N hydrochloric acid at 110° C. was shown in Table 15 below.

TABLE 15

Unit: μM/100 μM

| Amino acid | % | Amino acid | % |
| --- | --- | --- | --- |
| Aspartic acid | 7.8 | Methionine | 2.7 |
| Threonine | 7.6 | Isoleucin | 3.6 |
| Serine | 6.9 | Leucine | 7.6 |
| Glutamic acid | 8.8 | Tyrosine | 6.6 |
| Proline | 5.9 | Phenylalanine | 3.7 |
| Glycine | 9.3 | Lysine | 4.2 |
| Alanine | 9.2 | Histidine | 1.0 |
| Cystine/2 | 2.1 | Arginine | 6.2 |
| Valine | 6.8 | | |

(4) Isoelectric point:

The isoelectric point of the thus obtained active substance measured by comparing the electrophoretic pattern of the substance with those of standard proteins was 9.4.

(5) Specific rotatory power:

$[\alpha]_D^{25}$ of the substance obtained was $-29°$.

(6) Pattern of disc-electrophoresis:

In the disc-electrophoresis of the active substance under the conditions of:

Using polyacrylamide gel of concentration of 7.5% by weight, in a 1 N potassium hydroxide- glacial acetic acid buffer solution of pH of 4.3 containing 30 μg of the specimen under a current of 4 mA for 2 hours per one gel after staining with amide black and destaining by an aqueous 7% acetic acid solution, the active substance showed a sharp single band at a position of 2.3 cm of translocation (the edge of the spacer gel as the origin).

(7) Absorption of ultraviolet rays:

The specimen as a solution in distilled water at a concentration of 40 to 50 μg/ml showed a peak of absorption at $\lambda_{max}$ of 278 nm with log s of 4.72, the pH of solution being 6.3.

(8) Nuclear magnetic resonance spectrum:

The specimen as a solution in heavy water at a concentration of 10 mg/ml showed the following spectrum at room temperature:

$\delta 1.3 \sim 3.1$ ppm, $\delta 4.2 \sim 6.0$ ppm, and $\delta 6.8 \sim 8.7$ ppm.

Figure 14:
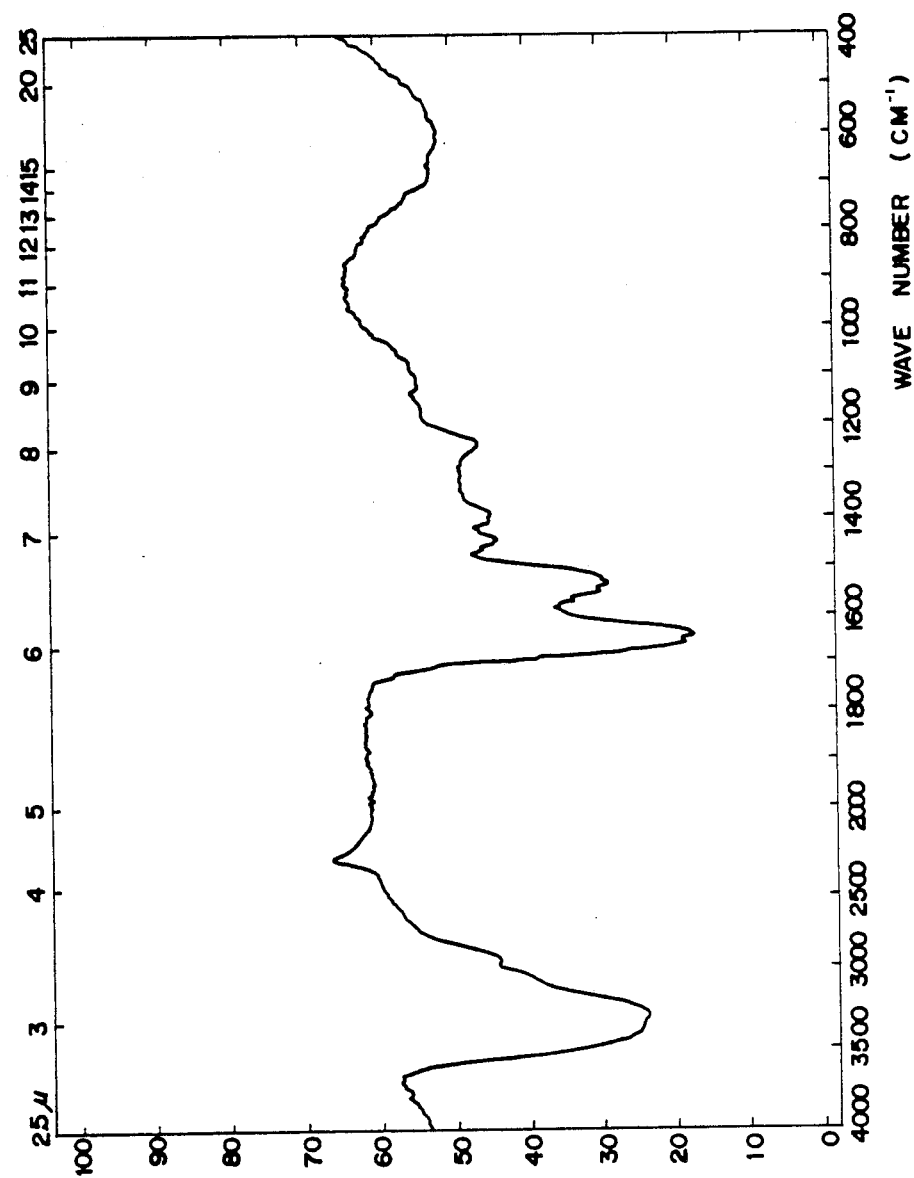

(9) Absorption of infrared rays:

The specimen as a mixed tablet with crystalline potassium bromide at a concentration of 1 mg/100 mg gave an infrared absorption spectrum shown in FIG. 14.

(10) Elementary analytical data:

About 15 to 20 mg of the specimen was dialyzed against distilled water for 4 to 5 days at 4° C., and then lyophyllized. The thus obtained powdery product was dried at 55° C. for 24 hours in a vacuum and subjected to elementary analysis, the data being as follows:

C:46.9%,
H:6.8%,
N:14.0% and
S:1.8%.

Note:

Preparation of the haptoglobin-sepharose column:

After activating 50 g of CNBr-(sepharose) (made by Pharmacia Company) by well washing with 1 mM hydrochloric acid, the activated sepharose was added to 100 ml of 0.1 M sodium hydrogen carbonate buffer solution of pH 8.3 which contained additionally 150 mg of haptoglobin and the mixture was brought into reaction for 3 hours at 23° C. Then, after washing the reaction product with 900 ml of 0.1 M sodium hydrogen carbonate buffer solution, the excess reactive groups were neutralized in 100 ml of 0.1 M boric acid buffer solution additionally containing 1 M ethanolamine of pH 9.0. After well washing the neutralizate with 0.1 M boric acid buffer solution of pH 8.1 additionally containing 0.5 M sodium chloride and with acetic acid buffer solution of pH 3.8 additionally containing 0.5 M sodium chloride in this order, the thus washed neutralizate was further washed with 0.1 M phosphate buffer solution of pH 7.0 additionally containing 0.5 M sodium chloride to be the haptoglobin-sepharose column for use in the purification of the substance of the present invention.

EXAMPLE 10

After adjusting 10 liter of the supernatant of a cultured medium in which the same bacterial strain as in Example 9 had been cultured in the same manner as in Example 9 with 1 N hydrochloric acid to pH 7.0, the thus adjusted supernatant was poured into a haptoglobin-sepharose column (5 cm × 20 cm) containing 784 mg of haptoglobin at a flow rate of 200 ml/hour.

Figure 15:
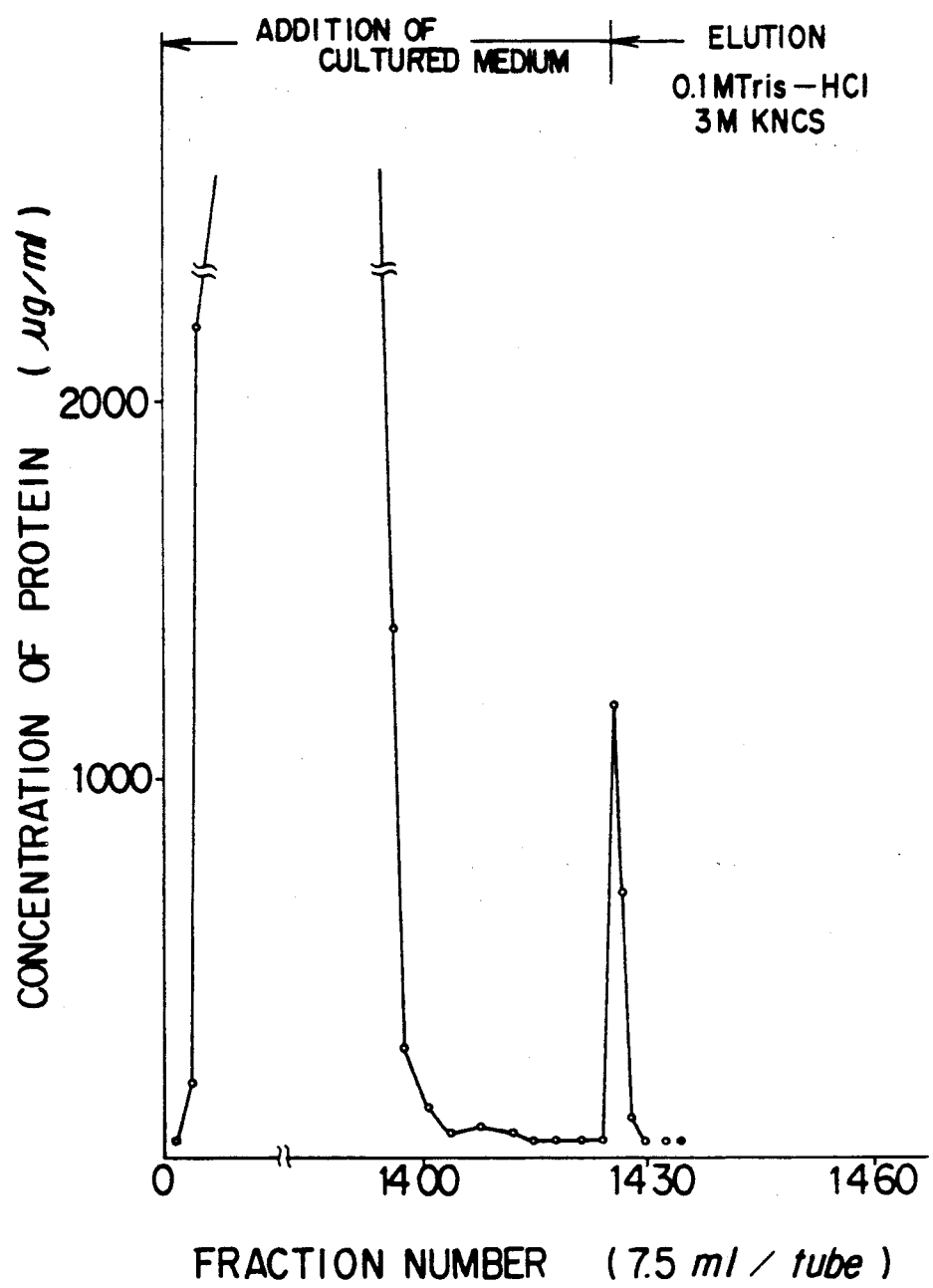

In this case, almost all proteins passed through the column without being adsorbed, and the object activity of promoting insulin-secretion was hardly detected in the eluate (refer to FIG. 15).

After thoroughly washing the column with 0 1 M trishydrochloric acid buffer solution of pH 8.0 additionally containing 0.5 M sodium chloride, the adsorbed protein onto the column was eluted by 0.1 M tris-hydrochloric acid buffer solution of pH 10.0 additionally containing 3 M of KNCS.

The thus obtained eluate was immediately introduced into dialyzer having a dialyzing membrane of the limiting molecular weight of 8000 (Catalogue Number: 3787-F-25, made by Thomas Company) and then the eluate was dialyzed against 10 liters of 0.05 M phosphate buffer solution additionally containing 2 M urea of pH 6.0, as the first step of purification.

Figure 16:
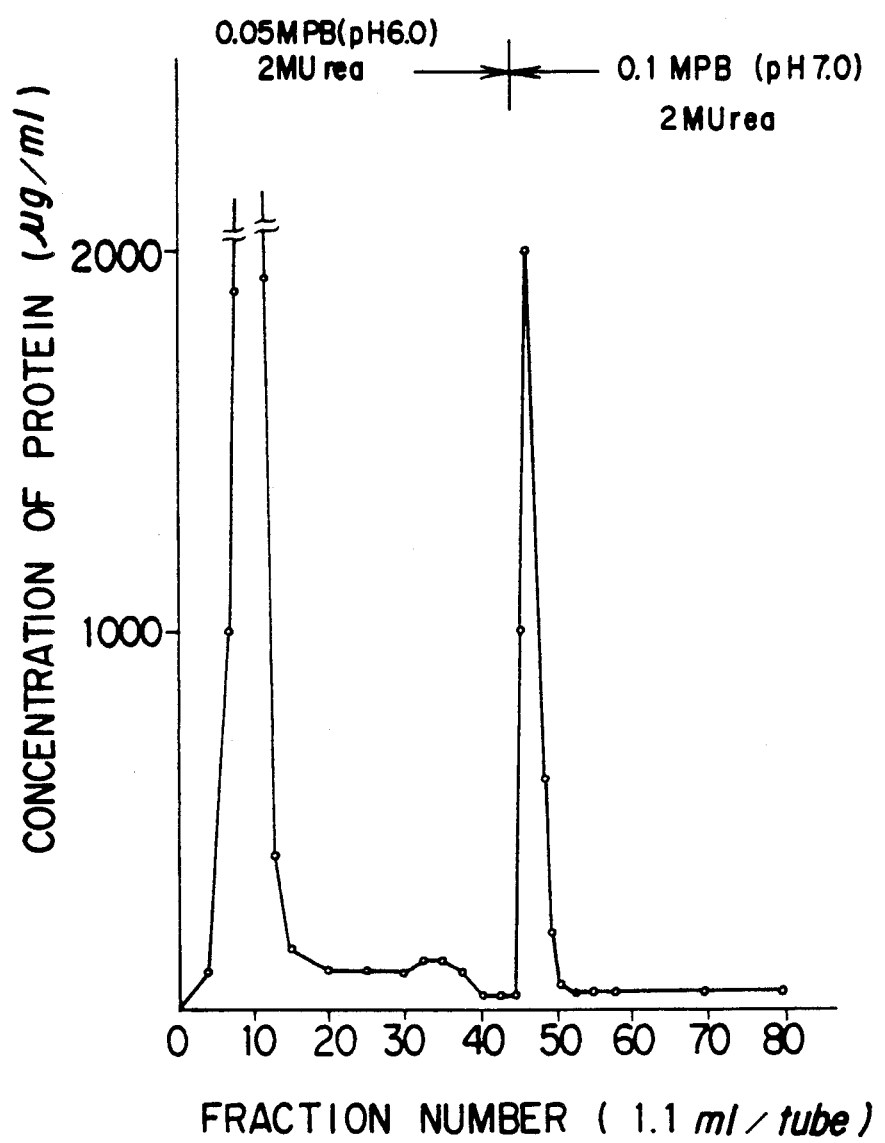
Figure 17:
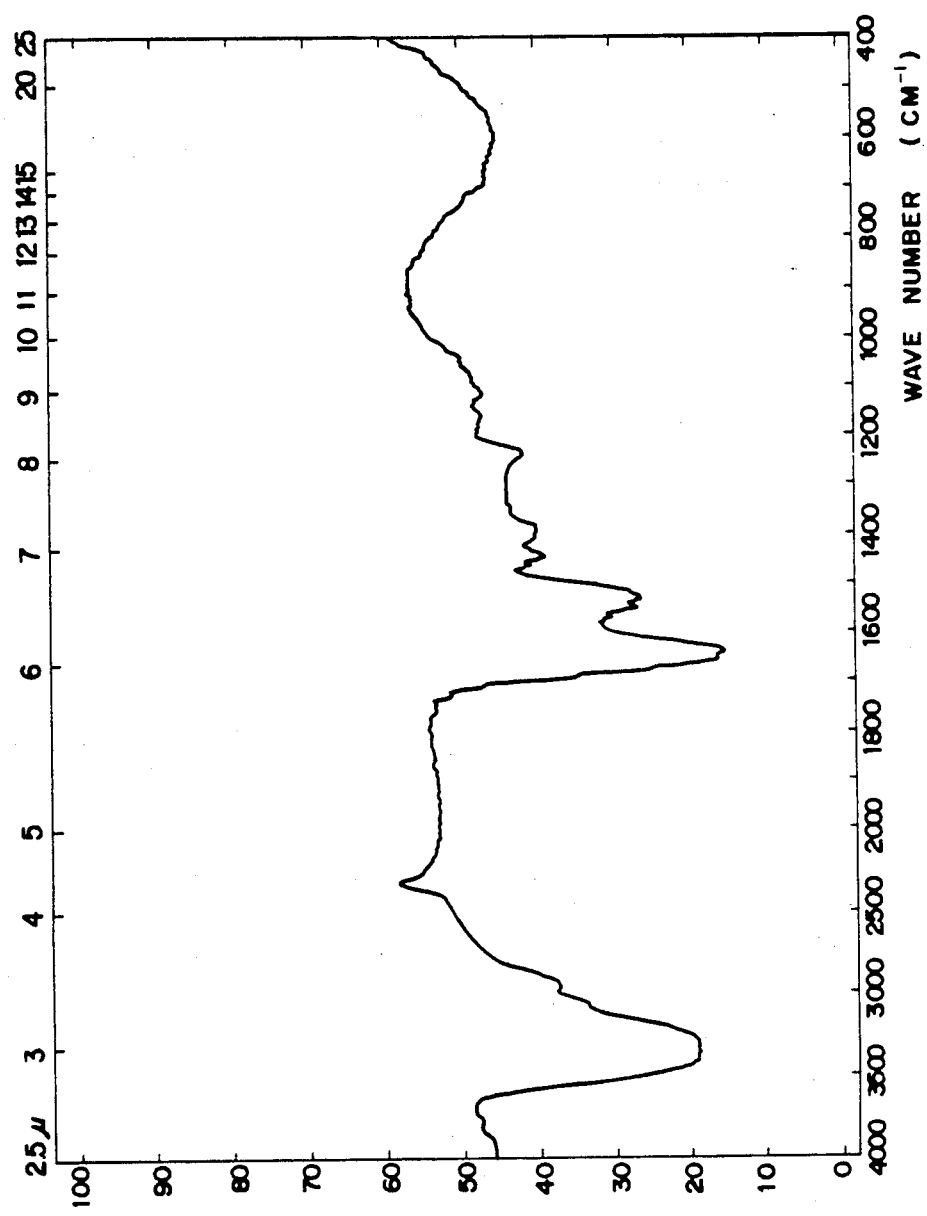

The dialyzate containing the active substance was condensed followed by passing through a carboxymethylsepharose CL-6B column (3 cm × 20 cm) equilibrated by 0.1 M phosphate buffer solution of pH 7.0 additionally containing 2 M of urea (refer to FIG. 16).

The specific activity and rate of purification, etc. of the thus purified active substance of promoting insulin secretion by the above-mentioned steps are illustrated in Table 16.

TABLE 16

| Step | Amount of solution (ml) | Amount of total protein (mg) | Specific activity (units/μg) | Rate of purification |
|---|---|---|---|---|
| Supernatant of cultured medium | 10,000 | 28,000 | 0.435 | 1 |
| After passing haptogrobin-sepahrose column | 15 | 14 | 435 | 1000 |
| After passing carboxymethyl-sepharose column | 4.27 | 3.8 | 1560 | 5928 |

(1) Molecular weight:
 (i) The molecular weight of the present product was approximately 67500 as measured by gel filtration.
 (ii) The molecular weight of the present product was 121,595±1,403 as determined by ultracentrifugal method.

(2) Sedimentation equilibrium constant:
6.7S.

(3) Content of proteins determined by Lowry's method:
Not less than 97% by weight.

(4) Composition of amino acid:

TABLE 17

| Amino acid | % | Amino acid | % |
|---|---|---|---|
| Aspartic acid | 7.8 | Methinine | 2.7 |
| Threonine | 7.6 | Isoleucine | 3.6 |
| Serine | 6.9 | Leucine | 7.6 |
| Glutamic acid | 8.8 | Tyrosine | 6.6 |
| Proline | 5.9 | Phenylalanine | 3.7 |
| Glycine | 9.3 | Lysine | 4.2 |
| Alanine | 9.2 | Histidine | 1.0 |
| Cystine/2 | 2.1 | Arginine | 6.2 |
| Valine | 6.8 | | |

Unit: μM/100 μM (5) Isoelectric point:
9.2

(6) Specific Rotatory power:
$[\alpha]_D^{25} = -28°$ (7) Disc-electrophoresis pattern:
The specimen showed an extremely sharp single band at a distance of 2.3 cm of translocation from the standard (the edge of the spacer gel).

(8) Absorption of ultraviolet rays:
The specimen of the product dissolved in distilled water at a concentration of 40 to 50 μg/ml gave an absorption maximum at 276 nm with a log ε of 4.69.

(9) Nuclear magnetic resonance spectrum:
The specimen dissolved in heavy water at a concentration of 10 mg/ml gave the following spectra at room temperature:

$\delta 1.3 \sim 3.4$ ppm, $\delta 4.3 \sim 5.9$ ppm, and $\delta 6.7 \sim 8.6$ ppm.

(10) Absorption of infrared rays:
The specimen after forming a tablet with potassium bromide at a concentration of 1 mg/100 mg gave an infrared absorption spectrum shown in FIG. 17.

(11) Elementary analytical data:
After dialyzing the specimen (15 to 20 mg) against distilled water for 4 to 5 days at 4° C. and then lyophylizing the thus obtained powdery product was dried at 55° C. for 24 hours under vacuum and subjected to elementary analysis to give the following data:
C:50.4%,
H:7.1%,
N:14.7% and
S:1.9%.

EXAMPLE 11:

After treating the supernatant of a cultured medium in which the same bacterial strain as in Example 9 had been cultured in the same manner as in Example 9 by the same procedures as in the first step of purification in Example 10, the thus obtained eluate was dialyzed against 10 liters of 0.1 M phosphate buffer solution of pH 7.0 additionally containing both 2 M urea and 0.5 M sodium chloride in a dialysis membrane with a limiting molecular weight of 3500 of Catalogue No. VT 351 made by Thomas Company.

After condensing the thus dialyzed solution containing the active substance of the present invention, the condensate was passed through a sephacryl S-200 column (1.5 cm × 100 cm), which had been equilibrated by 0.1 M phosphate buffer solution of pH 7.0 additionally containing both 2 M urea and 0.5 M sodium chloride to carry out the gel-filtration.

The specific activity, the rate of purification, etc. of the thus purified substance having activity of promoting insulin secretion are shown in Table 18 as follows.

TABLE 18

| Step | Amount of solution (ml) | Amount of total protein (mg) | Specific activity (units/μg) | Rate of purification |
|---|---|---|---|---|
| Supernatant of culture medium | 10,000 | 30,000 | 0.385 | 1 |
| After passing haptoglobin-sepharose column | 17 | 16 | 375 | 966 |
| After gel-filtration | 8.7 | 4.3 | 1400 | 3636 |

(1) Molecular weight:
 (i) The molecular weight of the present product was approximately 69,000 as measured by gel filtration.
 (ii) The molecular weight of the present product was 116,000±3,000 as determined by ultracentrifugal method.

(2) Sedimentation equilibrium constant:
6.5 S (3) Content of protein by the method of Lowry:
not less than 98% by weight.

(4) Composition of amino acid:

TABLE 19

| Amino acid | % | Amino acid | % |
|---|---|---|---|
| Aspartic acid | 7.5 | Methionine | 2.7 |
| Threonine | 7.4 | Isoleucine | 3.6 |
| Serine | 7.2 | Leucine | 7.4 |
| Glutamic acid | 10.0 | Tyrosine | 6.8 |
| Proline | 5.9 | Phenylalanine | 3.7 |
| Glycine | 9.5 | Lysine | 4.2 |
| Alanine | 9.0 | Histidine | 1.0 |
| Cystine/2 | 2.0 | Arginine | 6.2 |

TABLE 19-continued

| Amino acid | % | Amino acid | % |
|---|---|---|---|
| Valine | 6.9 | | |

(5) Isoelectric point (pH):
8.9

(6) Specific rotatory power:
$[\alpha]_D^{25} = -28°$ (7) Disc-electrophoresis pattern:

The specimen showed an extremely sharp single band at a distance of 2.2 cm from the edge of the spacer gel as the standard point.

(8) Absorption of ultraviolet rays:

The specimen dissolved in distilled water at a concentration of 40 to 50 μg/ml of pH 6.3 showed a maximum absorption band at 277 nm with a log ε of 4.82.

(9) Nuclear magnetic resonance spectrum:

The specimen dissolved in heavy water at a concentration of 10 mg/ml showed the following spectra:

$\delta 1.4 \sim 3.5$ ppm, $\delta 4.1 \sim 5.9$ ppm, and $\delta 6.8 \sim 8.7$ ppm.

Figure 18:
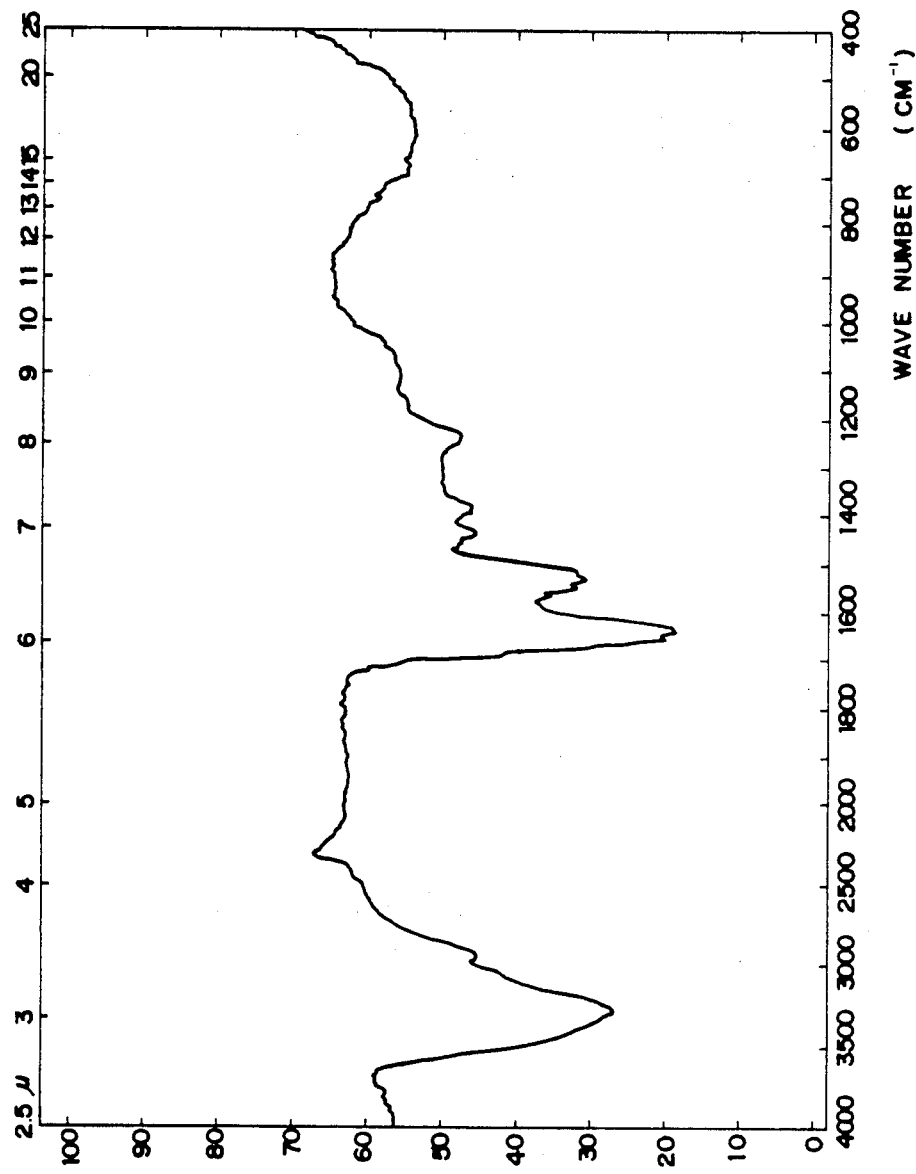

(10) Absorption of infrared rays:

The specimen formed into a tablet with potassium bromide at a concentration of 1 mg/100 mg showed a infrared absorption spectrum shown in FIG. 18.

(11) Elementary analytical data:

After dialyzing 15 to 20 mg of the specimen against distilled water for 4 hours at 4° C. and lyophyllizing the dialyzate, the lyophyllite was dried at 55° C. for 24 hours under vacuum to subject to elementary analysis giving the following data:
C:51.8%,
H:7.5%,
N:15.0% and
S:2.1%.

EXAMPLE 12:

Pharmacological properties of IAP - [I]

(12-1) Determination of the activity of promoting the secretion of insulin

The activity of IAP or fractions containing IAP in promoting the secretion of insulin, which is caused by one of various stimulants can be measured by determining the reaction of experimental animals and usually glucose is used as such a stimulant.

Test animals

Male Wistar rats of body weight of 130 to 140 g are used.

Test method

A specimen to be tested is dissolved in physiological saline solution, and 2 ml of the solution is injected into the femoral vein of a target rat fasted for 18 to 20 hours before the beginning of the test and kept under ether anesthesia. After 3 days, 0.1 ml of blood is collected from the caudal vein of the rat, immediately followed by the intraperitoneal injection of an aqueous 30% glucose solution at a dose rate of 1 ml/100 g of body weight. Acculately after 15 min, 0.1 ml of blood is collected again in the similar manner. The activity of the specimen in promoting the secretion of insulin, which is caused by glucose is obtained from the difference between the glucose levels in blood after and before the administration of glucose and the difference between the insulin levels after and before the administration of glucose.

Glucose level in blood is determined by the method of glucoseoxidase according to Bergmeyer and Bernet (refer to "Methods of Enzymatic Analysis", by Bergmeyer, H. U. Ed. Academic Press, USA, page 123(1963)).

Insulin level in blood is determined by the method of double antibody according to Morgan, C. R. and Razarow, A. (refer to "Diabetes" 12, 115(1963)).

Method for calculation of the activity of the specimen in promoting the secretion of insulin caused by glucose is as follows:

At first, the values of ΔI/ ΔG of the group of rats administered with the specimen, and of the control group of rats not administered with the specimen are obtained by the following formula:

$$\Delta I/\Delta G \ (\mu U/mg) = \frac{A - B \ (\mu U/ml)}{C - D \ (mg/ml)}$$

wherein A represents the level of insulin in blood after the administration of glucose (μU/ml); B represents the level of insulin in blood before the administration of glucose (μU/ml); C represents the glucose level in blood after the administration of glucose (mg/ml) and D represents the glucose level in blood before the administration of glucose.

The reasons of the use of the value of glucose level in blood at the calculation is that the level of insulin in blood is largely affected by the glucose level in blood.

Then, the unit of the specimen is obtained by the following calculation:

$$\text{Unit} = \frac{E - F}{F} \times 100$$

wherein E represents the mean an average value of ΔI/ΔG of the group of rats administered with the specimen, and F represents an average value of ΔI/ΔG of the control group of rats not administered with the specimen.

The specific activity of the specimen is defined as the quotient obtained by dividing the value of Unit by the amount of protein (IAP) according to the method of Lowry.

Table 20 shows the values of specific activity of IAP produced in Examples 1 to 11.

TABLE 20

| Example No. | Specific activity (Units/μg) |
|---|---|
| 1 | 429.0 |
| 2 | 930.0 |
| 3 | 890.0 |
| 4 | 920.0 |
| 5 | 1342.0 |
| 6 | 1349.0 |
| 7 | 505.0 |
| 8 | 380.0 |
| 9 | 1480.0 |
| 10 | 1560.0 |
| 11 | 1400.0 |

Dose-response relation

The dose-response relationship of the standard specimen of purified IAP obtained in Example 1 of the present invention is shown in Table 21 in which the dose is the amount of protein in the standard specimen of IAP, and the response is the mean value of the unit on five rats of the group.

TABLE 21

| Dose-Response Relationship of IAP | |
|---|---|
| Dose rate (ng/rat) | Response (Unit) |
| 8 | 62 |
| 16 | 53 |
| 32 | 54 |
| 63 | 81 |
| 125 | 104 |
| 250 | 129 |
| 500 | 208 |
| 1000 | 445 |
| 2000 | 571 |

Although the standard specimen of IAP shows a sigmoid-like relationship between dose and response, in the calculation of the unit of the standard specimen and of the unit of the fraction during the course of purification, the portion of the relationship as straight as possible (corresponding to the dose rate of 250 to 1000 ng/rat) has been selected.

(12-2) Summary of pharmacological effects of IAP

This substance (IAP) obtained in Example 1 is particularly noted for its prominent insulin secretion promoting activity but it also has other pharmacologically useful effects such as improvement of glucose tolerance, enhancement of insulin secretory response, promotion of healing of streptozotocin-induced diabetes and improvement of glucose tolerance of hereditary diabetes. Further, these activities sustain for several weeks to several months after a single administration of this substance. In view of the fact that the completely same phenomena were observed in the tested animals including mice, rats and dogs, it is considered that the pharmacological actions of this substance don't vary to any significant degree according to the difference in animal species.

It is considered that this substance finds its best application as a remedial medicine for diabetes. At present, medication for the diabetes depends on insulin injection or oral administration of antidiabetic drugs, but these are merely symptomatic treatments and, as things stand now, diabetes may be said an incurable disease. Further, the patient must go to hospital every day for insulin injection, and moreover, administration of the anti-diabetic drugs involves the danger of causing abnormal decline of the blood glucose level. The outstanding advantage of this substance is that it not only has per se a prominent insulin secretory activity but it also has the action to increase the insulin concentration in the blood only when the blood glucose level has been elevated under various conditions (hyperglycemic condition, especially at glucose loading such as during food ingestion) and to quickly return the elevated blood glucose value to the normal level Another salient advantage of this substance is that its activity sustains for the period of several weeks to even several months after a single administration. Therefore, in case the insulin secretory reaction to the blood glucose level has declined, administration of this substance provokes normal insulin secretory activity. Thanks to these properties, this substance finds a wider scope of applications, that is, it is not only useful as a remedial medicine for diabetes, complications thereof and geriatric diseases originating from diabetes, but it also proves effective in application to the prediabetes-stage ailment or as a preventive, remedial or diagnostic medicine for the juvenile diabetes for which no effective curative means is yet available.

(12-3) Insulin secretion promoting activity

This action is one of the remarkable actions of the present substance (IAP) obtained in Example 1 of which experiments were carried out on the rats (male rats of the Wistar strain) and dogs (both male and female dogs of Beagle strain).

Rats

The experimental conditions were same as used in measurement of activities described in Example (12-1), but in this experiment, the reactivity to the respective insulin secretion stimulants was measured on the third day after administration (1 microgram (as protein)/kg) of IAP to rats and compared with the normal rats (control) (Table 22). In challenge of glucose which is the most physiological factor a marked increase of insulin concentration in blood was seen over the control group notwithstanding the difference in route of glucose administration. A significant increase was also noted in reactivity to the hormone stimulants such as glucagon (1 mg/kg) and epinephrine (200μg/kg). There was also observed that insulin secretory activity of tolbutamide (200 mg/kg) and glibenclamide (2 mg/kg) which are currently in use clinically as antidiabetic drugs has been elevated by the administration of IAP. It was ascertained from these results that administration of the present active substance can markedly enhance the reactivity of the organism to the insulin secretion stimulants.

TABLE 22

| | Promotion of reactivity to various insulin stimulants in rats pre-treated with IAP | | | | | |
|---|---|---|---|---|---|---|
| | Control group | | | Treated group | | |
| | Before administration (μU/ml) | After administration (μU/ml) | Increment (μU/ml) | Before administration | After administration | Increment |
| Glucose p.o. 0.5 g 15 min. (*) | 16 ± 4 | 90 ± 4 | 74 | 25 ± 5 | 227 ± 47 | 202 |
| Glucose i.p. 0.3 g 15 min. | 26 ± 3 | 68 ± 12 | 42 | 55 ± 5 | 401 ± 114 | 346 |
| Glucose i.v. 0.05 g 15 min. | 16 ± 1 | 27 ± 3 | 11 | 25 ± 5 | 56 ± 6 | 31 |
| Glucagon i.v. 0.1 mg 5 min. | 24 ± 3 | 56 ± 5 | 32 | 28 ± 4 | 115 ± 3 | 87 |
| Epinephrine s.c. 0.1 mg 30 min. | 22 ± 5 | 29 ± 4 | 7 | 30 ± 3 | 102 ± 15 | 72 |
| Glibenclamide p.o. 0.2 mg 60 min. | 13 ± 4 | 52 ± 16 | 39 | 25 ± 3 | 82 ± 11 | 57 |
| Tolubutamide i.p. 20 mg | 23 ± 6 | 46 ± 8 | 23 | 55 ± 4 | 247 ± 73 | 192 |

TABLE 22-continued

| | Promotion of reactivity to various insulin stimulants in rats pre-treated with IAP | | | | | |
|---|---|---|---|---|---|---|
| | Control group | | | Treated group | | |
| | Before administration ($\mu$U/ml) | After administration ($\mu$U/ml) | Increment ($\mu$U/ml) | Before administration | After administration | Increment |
| 60 min. | | | | | | |

(Notes) (*):
The item means that glucose was orally administered at the rate of 0.5 g per 100 g of body weight of a rat, and blood specimen was sampled before and after 15 min of the administration.
Insulin concentration in blood in Table is the mean value and the standard error on five animals.

Dogs

IAP was administered intravenously to the dogs and after 3 days, glucagon (25 $\mu$g/kg body weight, intravenous injection) or glucose (0.3 g/kg body weight intravenous injection) stimulation was made to examine the insulin secretion promoting activity. The test animals were fasted for 18 hours before the experiment.

The experimental results from glucagon stimulation are shown in Table 23. Promotion, though slight, of insulin secretion was noted over the control 5 minutes after glucagon administration at a dose of 50 ng (as protein, same in the following unless otherwise specified)/kg (body weight), and insulin secretion was promoted proportionally to the increase of dose of IAP, reaching substantially the highest reaction at the dose rate of 1 $\mu$g/kg. Similar potentiation of the insulin secretory activity was noticed in glucose (oral and intravenous administrations) and epinephrine challenges (Table 24). These results indicate that noticeable enhancement of reactivity to the insulin secretion stimulants is induced in the dogs too, by administration of IAP.

TABLE 23

| Insulin secretion potentiation after administration of glucagon to dogs pretreated with IAP | | | | | | |
|---|---|---|---|---|---|---|
| | Insulin concentration in blood after the following minutes of administration of glucagon ($\mu$U/ml) | | | | | |
| Dose rate of IAP | 0 | 5 | 15 | 30 | 45 | 60 |
| Control group | 3 | 31 | 32 | 16 | 10 | 8 |
| Treated group | | | | | | |
| 0.05 $\mu$g/kg | 2 | 50 | 43 | 18 | 17 | 6 |
| 0.1 | 3 | 73 | 37 | 9 | 5 | 2 |
| 0.5 | 3 | 196 | 100 | 24 | 11 | 5 |
| 1.0 | 2 | 360 | 230 | 10 | 13 | 7 |
| 2.0 | 2 | 320 | 60 | 19 | 6 | 8 |

(Note): $\mu$U/ml mean from 3 animals in respective cases.

TABLE 24

| Enhancement of insulin secretion after respective challenges of glucose and epinephrine on dogs pretreated with IAP | | |
|---|---|---|
| | Insulin concentration in blood ($\mu$U/ml) | |
| | Before challenge of stimulant | After challenge of stimulant |
| Control group | 6 ± 1 | 20 ± 9 |
| Glucose after 5 minutes of intravenous injection | | |
| Treated group | 7 ± 1 | 89 ± 36 |
| Control group | 8 ± 1 | 8 ± 1 |
| Epinephrine after 5 minutes of intravenous injection | | |
| Treated group | 18 ± 6 | 225 ± 28 |

Note: $\mu$U/ml mean ±SE from 3 animals in respective cases.

(12-4) Glucose tolerance improving activity

Glucose was loaded orally to the rats and the dogs, and attenuation of blood glucose level and insulin concentration in blood after glucose loading were measured to determine glucose tolerance. The glucose was given to rats at a dose 0.5 g/100 g body weight and to dogs at a dose of 15 g/dog after 18- to 20-hour fasting.

In the respective groups of rat and dog treated with intravenous injection of IAP obtained in Example 1, at respective dose rates of 0.5 $\mu$g (as protein)/Kg and 1 $\mu$g (as protein)/Kg 3 days before the experiment, the rise of glucose level in blood was remarkably suppressed, while there was a conspicuous increase of insulin concentration in blood, and the insulin concentration was quickly returned to the level before glucose loading in correspondence to normalization of blood glucose level, and no decline of blood glucose level due to excessive secretion of insulin was seen (Tables 25 and 26). These results manifest marked improvement of glucose tolerance in the animals treated with IAP.

TABLE 25

| | Changes in concentrations of blood glucose and plasma insulin of dogs after glucose loading | | | | | | |
|---|---|---|---|---|---|---|---|
| | Time after glucose loading (minute) | | | | | | |
| | 0 | 15 | 30 | 60 | 90 | 120 | 180 |
| Blood glucose (mg/dl) | | | | | | | |
| Control group | 125 ± 9 | 177 ± 14 | 123 ± 9 | 118 ± 4 | 111 ± 19 | 113 ± 13 | 109 ± 1 |
| Treated group | 97 ± 3 | 117 ± 9 | 108 ± 7 | 118 ± 4 | 96 ± 6 | 88 ± 8 | 97 ± 3 |
| Plasma insulin ($\mu$U/ml) | | | | | | | |
| Control group | 3 ± 2 | 17 ± 2 | 23 ± 15 | 8 ± 2 | 12 ± 2 | 8 ± 3 | 8 ± 1 |

TABLE 25-continued

| | Changes in concentrations of blood glucose and plasma insulin of dogs after glucose loading | | | | | | |
|---|---|---|---|---|---|---|---|
| | Time after glucose loading (minute) | | | | | | |
| | 0 | 15 | 30 | 60 | 90 | 120 | 180 |
| Treated group | 9 ± 5 | 63 ± 10 | 16 ± 6 | 20 ± 2 | 12 ± 4 | 9 ± 1 | 10 ± 1 |

The treated group was injected intravenously with 1 μg (protein) of IAP/kg 3 days before the experiment.
Mean ± SE from 4 animals in respective cases.

TABLE 26

| | Changes in concentrations of blood glucose and plasma insulin of rats after glucose loading | | | | | |
|---|---|---|---|---|---|---|
| | Time after glucose loading (minute) | | | | | |
| | 0 | 30 | 60 | 90 | 120 | 180 |
| Blood glucose (mg/dl) | | | | | | |
| Control group | 68 ± 1 | 102 ± 9 | 98 ± 3 | 108 ± 4 | 114 ± 4 | 120 ± 4 |
| Treated group | 51 ± 1 | 72 ± 6 | 54 ± 2 | 48 ± 5 | 62 ± 6 | 69 ± 7 |
| Plasma insulin (μU/ml) | | | | | | |
| Control group | 19 ± 2 | 47 ± 6 | 38 ± 4 | 41 ± 2 | 41 ± 5 | 55 ± 5 |
| Treated group | 25 ± 4 | 126 ± 9 | 79 ± 10 | 61 ± 6 | 69 ± 7 | 104 ± 18 |

The treated group was injected intravenously with 0.5 μg of IAP 3 days before this experiment.
Mean ± SF from 5 animals in respective case.

(12-5) Recovery of streptozotocin-induced diabetes by pretreatment with IAP

It is known that the challenge of streptozotocin (hereinafter referred to as STZ) induces the diabetes to the experimental animals by remarkably destroying β-cell of the island of Langerhans. However it was found that in IAP-treated rats, the STZ-induced diabetes was cured promptly and the blood glucose and blood tolerance at non-fast state were normalized.

The experiment was carried out in such a method that IAP obtained in Example 1, was administered to rats at a dose of 1 μg/animal and after 3 to 5 days, STZ was administered intravenously at a dose rate of 5 mg/100 g body weight.

After 24 hours from the administration of STZ the hyperglycemia was observed both in the control and treated groups however in the treated group the blood glucose level approached to the normal region on the fifth and seventh days gradually after administration of STZ and the concentration of plasma insulin was also significantly higher than that of the control group (Table 27).

Further on the seventh day after administration of STZ, the glucose loading experiment was carried out and the glucose tolerance was also studied (Table 28). If these rats were fasted, the concentration of blood glucose became the same apparently both in the control (administered only with STZ) and the IAP-treated groups, however the deterioration of glucose tolerance was clearly observed in the control group in comparison with the normal group (not treated).

On the other hand, in the treated group the glucose tolerance was improved to such a degree as comparable to that of the normal group and the plasma insulin in response to glucose loading was higher than that of the control group. From the above findings, it may be considered that the STZ-induced diabetes is cured in the animals pre-treated with IAP.

TABLE 27

| | Recovery from streptozotocin diabetes by pretreatment with IAP | | | | |
|---|---|---|---|---|---|
| | Number of days after administration of STZ | | | | |
| | 0 | 2 | 3 | 5 | 7 |
| Control group | | | | | |
| Blood glucose (mg/dl) | 94 ± 3 | 375 ± 20 | 360 ± 16 | 355 ± 8 | 352 ± 4 |
| Plasma insulin (μU/ml) | 20 ± 2 | 30 ± 3 | 26 ± 4 | — | 24 ± 2 |
| Treated group | | | | | |
| Blood glucose (mg/dl) | 98 ± 2 | 358 ± 19 | 250 ± 35 | 199 ± 41 | 145 ± 22 |
| Plasma insulin (μU/ml) | 63 ± 5 | 69 ± 5 | 54 ± 6 | — | 62 ± 4 |

(Note): Mean ± SE from 5 animals in respective cases.

TABLE 28

| | Glucose tolerance improvement in streptozotocin diabetes by pre-treatment with IAP | | | | |
|---|---|---|---|---|---|
| | Time after glucose loading (minute) | | | | |
| | 0 | 15 | 30 | 60 | 90 |
| Control group | 83 ± 7* | 214 ± 18 | 291 ± 27 | 327 ± 23 | 264 ± 32 |
| | (18 ± 2)** | (22 ± 5) | | | |
| Treated group | 82 ± 6 | 159 ± 16 | 177 ± 14 | 173 ± 10 | 141 ± 13 |
| | (24 ± 2) | (49 ± 2) | | | |
| Normal group | 82 ± 3 | 130 ± 11 | 161 ± 5 | 155 ± 4 | 138 ± 7 |
| | (17 ± 1) | (43 ± 4) | | | |

*Blood glucose (mg/dl)
**Plasma insulin (μU/ml)
Mean ± SE from 5 animals in respective cases.

(12-6) Improvement of glucose tolerance by IAP administration to spontaneous diabetic mice (KK mice) similar to human diabetes KK mouse is considered to be the model animal of pathosis similar to the diabetes of human being since the mice get spontaneous diabetes with their aging while having hereditary and environmental factors as the background. Therefore, whether the therapeutic effect of IAP obtained in Example 1, is effecacious or not to this animal will be a big index on analogizing the case of human being from the results obtained from the animal experiment. Consequently the following experiment was carried out. The mice used for the experiment were KK mice which were originally supplied from the Faculty of Agriculture, Nagoya University, on which mating between their brothers and sisters as well as their breeding were continued. The experiment was carried out in the following way. The glucose was loaded by oral administration (0.15 g/20 g body weight) to the mice of 20-25 week old, next 5 animals which showed a definite deterioration in glucose tolerance in comparison with the normal group (ddY strain) were selected. As shown in Table 29, disappearance of glucose after glucose loading was not observed in these mice and they are evidently considered to be in the diabetic state. To this KK mice group, the glucose was loaded again on the third day after injection of the present substance into the tail vein. As the result, the glucose tolerance increased greatly as compared with the state before administration of the present substance. Further the glucose tolerance was improved much better than that of the normal group. Consequently it may be considered that the administration of IAP results in the satisfactory therapeutical effect to the spontaneous diabetes.

TABLE 29

Improvement of glucose tolerance in KK mice by IAP treatment

| Group of treatment | Blood glucose level (mg/dl) after the under mentioned time (min.) | | | | |
|---|---|---|---|---|---|
| | 0 | 30 | 60 | 120 | 180 |
| Normal group (ddY strain) | 98 ± 7 | 214 ± 16 | 339 ± 13 | 192 ± 9 | 144 ± 14 |
| Diabetic group (KK strain) | | | | | |
| Before treatment | 117 ± 6 | 300 ± 33 | 308 ± 21 | 326 ± 40 | 310 ± 39 |
| After treatment | 72 ± 3 | 150 ± 11 | 118 ± 9 | 90 ± 8 | 63 ± 11 |

Mean ± SE from 5 animals in respective cases.

(12-7) Anti-diabetic effect

Spontaneous diabetic animal, KK mice, were used to investigate the anti-diabetic activity of each sample. Each sample was injected intravenously into KK mice at a dose of 0.1 and 0.5 µg/mice and blood-concentration of glucose were examined before 3 and 10 days after the injection.

The results of anti-diabetic effect are shown in Table 30 below.

TABLE 30

| Example No. | dose (µg/mice) | Blood-concentration of glucose (mg/dl), after days of administration | | |
|---|---|---|---|---|
| | | 0 | 3 | 10 |
| Control | 0 | 352 ± 18 | 362 ± 20 | 349 ± 9 |
| 1 | 0.1 | 361 ± 12 | 278 ± 18* | 302 ± 13* |
| | 0.5 | 348 ± 9 | 234 ± 15** | 256 ± 7** |
| 2 | 0.1 | 360 ± 23 | 255 ± 9** | 249 ± 12** |
| | 0.5 | 371 ± 11 | 183 ± 12** | 201 ± 6*** |
| 3 | 0.1 | 349 ± 15 | 260 ± 8** | 241 ± 7*** |
| | 0.5 | 332 ± 9 | 163 ± 14** | 169 ± 12*** |
| 4 | 0.1 | 360 ± 10 | 260 ± 17* | 283 ± 9** |
| | 0.5 | 352 ± 12 | 188 ± 3** | 197 ± 15*** |

TABLE 30-continued

| Example No. | dose (µg/mice) | Blood-concentration of glucose (mg/dl), after days of administration | | |
|---|---|---|---|---|
| | | 0 | 3 | 10 |
| 5 | 0.1 | 342 ± 5 | 231 ± 21* | 212 ± 16** |
| | 0.5 | 344 ± 12 | 152 ± 5*** | 162 ± 5*** |
| 6 | 0.1 | 360 ± 17 | 206 ± 11** | 203 ± 9*** |
| | 0.5 | 349 ± 7 | 158 ± 13** | 161 ± 7*** |
| 7 | 0.1 | 361 ± 9 | 302 ± 12$^{NS}$ | 291 ± 14* |
| | 0.5 | 358 ± 10 | 228 ± 17** | 230 ± 6*** |
| 8 | 0.1 | 341 ± 7 | 299 ± 13$^{NS}$ | 288 ± 15* |
| | 0.5 | 352 ± 13 | 229 ± 15** | 241 ± 19** |

The number of observations is three.
*p < 0.05, p < 0.01, *p < 0.001

(12-8) Duration of pharmacological action

The pharmacological activities of IAP obtained in Example 1, come to manifest themselves in several hours after administration, reach the highest levels in 3 to 7 days and then gradually decline Shown below are the results of experiments on duration of activities of IAP in rats (0.5 µg) and dogs (1.0 µg/kg).

In the dogs, the investigations were made on the glucose tolerance in response to glucose loading by intravenous injection on the 15th day after IAP administration and also on the insulin secretion activities in response to the administration of epinephrine and glucagon on 29th and 42nd days respectively after IAP administration. The results on the intravenous administration of glucose at a dose rate of 25 µg/Kg is shown in Table 31. As the result, sufficient activities were still observed on 42nd day. In the rats, about 50% of the activity at the maximum (3 days after administration) was observed on 28th day after administration.

It is judged from these results that the pharmacological activities of IAP sustain for several weeks to several months although the strength of such activities is uncertain for the reason of dosage.

TABLE 31

Increase in insulin secretion in dogs by glucagon challenge on 42nd day after IAP administration

| Time after glucagon challenge (minute) | Insulin concentration in blood (µU/ml) | | | |
|---|---|---|---|---|
| | 0 | 5 | 15 | 30 |
| Control group | 6 ± 1 | 14 ± 1 | 9 ± 2 | 8 ± 1 |
| Treated group | 6 ± 1 | 71 ± 9 | 28 ± 8 | 7 ± 1 |

Intravenous injection with 25 µg/kg of glucagon Mean ± SE from 5 animals in respective cases.

(12-9) Effective and therapeutically acceptable dose and route of administration The effective and therapeutically acceptable dose of IAP for human application is in a range of 10 ng/kg (body weight) 100 µg/kg (body weight) in case of the purified product.

The most effective method of administration is the intravenous injection, however other modes of administration are also available.

(12-10) Stability of activity

Thermal stability
Method of experiment:

The solution of IAP obtained in Example 1 (40 µg as protein/ml, pH 7.0) was exposed to various temperatures from 37° C. to 100° C. for 15 minutes and the change in insulin secretion promoting activity was studied. As the control, the specimen kept at 4° C. was used and the change of activity is shown in Table 32 by the relative activity as compared with the activity of specimen kept at 0° C. for 15 min.

TABLE 32

| Temperature (°C.) | Relative activity |
| --- | --- |
| 4 | 100 |
| 37 | 100 |
| 56 | 113 |
| 60 | 76 |
| 70 | 53 |
| 80 | 18 |
| 100 | 13 |

As is seen in Table 32, although the region of thermal stability of IAP is below 56° C., the activity was still observed in the solution kept at 80° C.

Stability of the activity to various pH

The solution of 40 μg protein/ml was added with 3 N HCl or 3 N NaOH to adjust pH and was stored at 4° C. for 24 hours. Afterwards the resultant solution was administered to the animals after returning its pH near to neutrality and changes in insulin secretion promoting activity were studied. The results are indicated by the relative activities with pH 7.0 as 100 as shown in Table 33.

The pH of an aqueous solution of IAP at a concentration of 40 micrograms (as protein)/ml was adjusted to the respective values in Table 17 by the addition of either aqueous 3N hydrochloric acid solution or aqueous 3N sodium hydroxide solution, and the solution was kept at 4° C. for 24 hours. Then the pH of the solution was returned to nearly neutral and the solution, was administered to experimental animals for observing the change of its activity in promoting the insulin secretion. The results are shown in Table 33 which indicates the change of the activity by the relative activity as compared to the activity of the solution kept at a pH of 7.0.

TABLE 33

| pH | Relative activity |
| --- | --- |
| 1 | 16 |
| 2 | 27 |
| 3 | 43 |
| 4 | 112 |
| 7 | 100 |
| 9 | 120 |
| 10 | 89 |
| 11 | 23 |
| 12 | 0 |

As is seen Table 33, although IAP is stable in the range of pH 4 to 9, the activity survived in the solutions of pH lower than 3 and also in those of pH 10 and 11.

(12-11) Acute toxicity

The following Table 34 shows the acute toxicity $LD_{50}$ (μg/kg body weight), of the purified IAP sample when the mice of ddY strain were used as experimental animals.

TABLE 34

| | $LD_{50}$ in ddY mice | | | |
| --- | --- | --- | --- | --- |
| Example No. | $LD_{50}$ (μg/Kg) (intravenous injection) | | $LD_{50}$ (μg/kg) (subcutaneous injection) | |
| | ♂ | ♀ | ♂ | ♀ |
| 1 | 222 | 155 | 540 | 580 |
| 2 | 198 | 143 | — | — |
| 3 | 205 | 138 | — | — |

TABLE 34-continued

| | $LD_{50}$ in ddY mice | | | |
| --- | --- | --- | --- | --- |
| Example No. | $LD_{50}$ (μg/Kg) (intravenous injection) | | $LD_{50}$ (μg/kg) (subcutaneous injection) | |
| | ♂ | ♀ | ♂ | ♀ |
| 4 | 228 | 161 | — | — |
| 5 | 203 | 140 | — | — |
| 6 | 216 | 172 | — | — |
| 7 | 230 | 168 | — | — |
| 8 | 252 | 179 | — | — |

(12-12) Pharmaceutical applications

As described in detail hereinabove, the novel protenic active substances according to this invention are very useful as remedial and preventive medicines for diabetes. The effective dose for human applications varies depending on specific activity of the active substances. Usually, for use in promotion of insulin promoting secretory activity, they are administered within the amount ranging from 10 ng/kg (body weight) to 100 μg/kg (body weight).

As for the way of administration to the patient intravenous injection is most effective in every use, but there may as well be employed other modes of administration such as intraperitoneal, intramuscular or subcutaneous injection, direct administration into the digestive organs, or oral, intrarectal, sublingual, nasal mucosal, intraarterial intralymphangial or intratracheal administration.

As regards the form of administration there may be cited injections, suppositories, enteric and gastric coatings, sublingual tablets and inhalants. A most simple example of injection compositions is a 1-ml mixture of 10,000 units of insulin secretory active substance (IAP), 9 mg of sodium chloride and sterile distilled water.

It will be apparent to those skilled in the art that other additives having no possibility of affecting the activity of the active substance may be suitably mixed in preparation of medicaments.

EXAMPLE 13:

Pharmacological properties or Islets-Activating Protein [II]

(13-1) Antihypertensive Activity of IAP

The antihypertensive activity of IAP obtained in Example 1 was examined by using the spotaneous hypertensive male rats of strain SHR derived from those sent from the Department of Pathology, University of Kyoto, School of Medicine, especially on those showing the systolic blood pressure of higher than 190 mmHg.

IAP was administered by intravenation after diluting with a physiological saline solution at the dose rate of 1 microgram or 10 micrograms per kg body weight. Only the physiological saline solution was given in the same manner to control.

The determination of the systolic blood pressure of the rat was carried out by using an electrosphygmomanometer (made by Narco Biosystem Co. Model PE-300) on the rat warmed at a temperature of 40° C for 5 minutes in advance of the determination without anesthesia. The results of determination are shown in Table 35 as well as in FIG. 19.

As are seen in Table 35 and FIG. 19, a significant depression of blood pressure as compared to control was observed respectively after 7 and 35 days of the intravenation of IAP once at a dose rate of 1 microgram per kg body weight on the rat. In the case where 10 micrograms on IAP/kg were intravenated to the rat, a continuous antihypertensive activity of IAP appeared on the treated rat as compared to control showing the continuously depressed state of blood pressure for more than one month.

According to the above-mentioned results it is considered that IAP is effective in the treatment of hypertension because it exhibits a remarkable pharmacological effect of improving hypertension for a long period of time after only one administration.

EXAMPLE 14:

Therapeutical effect of the substance of the present invention against diabetes mellitus on KK-mouse.

Since spontaneous occurrence of diabetes mellitus is found on KK-strain of mouse with aging with genetic and environmental factors as its background, it is considered as the model animal in pathosis similar to diabetes mellitus of human beings. Accordingly, in consideration that whether the therapeutical effect of the substance of the present invention appears on experimental animals or not might be an important index in the case where the results of animal experiment is analogized on human beings, the following experiments were undertaken.

TABLE 35

Antihypertensive Activity of IAP appeared on Spontaneous Hypertensive SHR Rats Sistolic blood pressure mmHg

| Rats strain SHR | Before administration | After days of administration | | | | | | |
|---|---|---|---|---|---|---|---|---|
| | | 3 | 7 | 14 | 21 | 28 | 35 | 42 |
| Control | 203 ± 3 | 198 ± 3 | 204 ± 4 | 210 ± 5 | 213 ± 4 | 208 ± 4 | 219 ± 3 | 209 ± 3 |
| Admin. IAP at 1 g/kg | 204 ± 1 | 197 ± 3 | 186 ± 3** | 205 ± 3 | 205 ± 4 | 211 ± 4 | 201 ± 6* | 209 ± 4 |
| Admin. IAP at 10 g/kg | 204 ± 3 | 138 ± 6*** | 141 ± 7*** | 157 ± 5*** | 158 ± 5*** | 148 ± 4*** | 159 ± 3*** | 163 ± 5*** |

Notes:
(1) Each value of the systolic blood pressure represents the mean value with standard error on ten rats of each group.
(2) The mean value of the systolic blood pressure of normal rat was 135 ± 3 mmHg.
(3) Asterisc shows the degree of significance as compared to control and *means $P < 0.05$; means $P < 0.01$; and *means $P < 0.001$.

(13-2) Effects of IAP on the Blood Pressure of normal rats METHODS OF DETERMINATION OF THE EFFECTS The blood pressure and heart rate of the male Wistar rats of age of 5 weeks before and after administering IAP obtained in Example 1 into vena caudalis of each individuals of 8 rats forming a group were determined by the same method.

RESULTS (1) Blood Pressure:

Although the blood pressure did not show any change after 3, 6 and 9 hours of the administration, a depression was observed after 24 hours at the respective dosages of 3 and 10 micrograms/kg b.w.

The effect of IAP of the blood pressure appearing with the lapse of time was as follows:

(i) At 1 microgram/kg, a depression was observed on the second and third day of the administration.

(ii) At 3 micrograms/kg, the depression of the blood pressure continued until the 14th day after the administration and (iii) At 10 micrograms/kg, the blood pressure was depressed to 86.6 mmHg at the first day of the administration and then showed a tendency to recover until the third day, however, at the seventh day, showed a depression which lasted significantly as compared to control until after 21 days of the administration (FIG. 20).

Of the mice of KK-strain which had originally been supplied by the domestic animal breeding laboratory of the Faculty of Agriculture, Nagoya University, and on which mating was carried out at a coefficient of inbreeding of ¼ continuously with breeding after 20 to 25 weeks of their birth with body weight of about 40 g, 20 mice were selected by glucose-loading test, which showed the blood sugar level of higher than 300 mg/dl in non-fasting state and showed the positivity in glucosuria test. They were divided into 4 groups, the group being consisted of 5 animals. Into each of the three groups, each of the active substances obtained in Examples 9, 10 and 11 was injected from the caudal vein at a rate of 0.1 µg/mouse. Into the remaining one group, a physiological saline solution was injected from the caudal vein as control. The levels of blood sugar and urine sugar of the thus treated mice were measured weekly for 3 weeks, and the mean levels are shown in Table 36.

The level of blood sugar was measured by the glucoseoxidase method, and the level of urine sugar was measured by Labstics $^R$- method (registered by Miles and Sankyo). In Table 36, the percentage of urine sugar is the number of animals showed +++ or higher than +++ of urine sugar divided by the number of animals of the group (five) and multiplied by 100.

TABLE 36

| Substance administered | | Before administration | After days of administration | | | |
|---|---|---|---|---|---|---|
| | | | 3 | 7 | 14 | 21 |
| Substance of Example 9 | Blood sugar level (mg/dl) | 368 ± 9 | 218 ± 13 | 192 ± 9 | 189 ± 13 | 212 ± 10 |
| | Urine sugar level (%) | 100 | 40 | 0 | 0 | 20 |
| Substance of Example 10 | Blood sugar level (mg/dl) | 352 ± 13 | 228 ± 21 | 183 ± 16 | 182 ± 15 | 199 ± 11 |
| | Urine sugar level (%) | 100 | 40 | 0 | 0 | 20 |
| Substance of Example 11 | Blood sugar level (mg/ml) | 372 ± 21 | 203 ± 19 | 178 ± 9 | 194 ± 9 | 218 ± 16 |

TABLE 36-continued

| Substance administered | | Before administration | After days of administration | | | |
|---|---|---|---|---|---|---|
| | | | 3 | 7 | 14 | 21 |
| | Urine sugar level (%) | 100 | 20 | 0 | 0 | 40 |
| Physiological saline solution (control) | Blood sugar level (mg/ml) | 380 ± 15 | 368 ± 21 | 362 ± 13 | 395 ± 8 | 391 ± 17 |
| | Urine sugar level (%) | 100 | 100 | 100 | 100 | 100 |

Acute toxicity of the substance of the present invention to mammals

The acute toxicity of each of the substances of the present invention obtained Examples 9, 10 and 11, respectively was tested using mice of ddY-strain by intravenal injection. Table 37 shows the results of the test as $LD_{50}$ (μg/kg body weight).

TABLE 37

| | $LD_{50}$ (μg/kg body weight) | |
|---|---|---|
| Substance | male | female |
| Substance of Example 9 | 231 | 155 |
| Substance of Example 10 | 229 | 154 |
| Substance of Example 11 | 230 | 155 |

What is claimed is

1. A biologically active substance consisting essentially of purified Islets-Activating Protein having insulin secretion promoting action, obtained by culturing at least one pathogenic strain of the microorganism Bordetella pertussis (Phase I or Phase II) in a culture medium therefor and collecting and purifying the cultured cells and/or culture medium by at least one method selected from the group consisting of the chromatographic method, the molecular sieve method, the electrophoretic method, and the biological method, to recover said biologically active substance having the following properties:

a molecular weight of 73,000±11,000 as determined by gel filtration;
a protein content as determined by Lowry's method of not less than 95% by weight;
the glucide content by the phenol-$H_2SO_4$ method of less than 2% by weight;
the lipid content being lower than the limit of detection;
percentile amino acid composition of the protein moiety (average ratio, μM/100 μM) being: aspartic acid, 7.5–7.9; threonine, 6.8–7.8; serine, 5.9–7.6; glutamic acid, 8.8–10.0; proline, 5.5–6.4; glycine, 8.7–9.6; alanine, 9.0–10.8; cysteine/2,1.0–2.5; valine 6.5–7.6; methionine, 2.5–3.3; isoleucine, 3.6–4.6; leucine, 7.4–8.7; tyrosine, 5.1–6.8 phenylalanine, 3.7–4.5; lysine, 3.1–4.4; histidine, 0.9–1.5; and arginine, 6.1–6.6;
disc electrophoretic pattern: acrylamide (polyacrylamide) concentration, 7.5%; in a 1N KOH-glacial acetic acid buffer (pH 4.3) disc electrophoresis of said substance giving a very sharp single band on the cathode side;
hdyroxyapatite column chromatographic pattern: said substance in 0.1 M phosphate buffer (pH 7.0) being adsorbed on said column and the adsorbed substance being eluted with 0.1 M phosphate buffer (pH 7.0) containing 0.5 M NaCl;
isolectric point $[\alpha]_D^{25} = -29° \pm 5°$; and,
said substance having insulin secretion promoting activity of not less than 380 units/μg as well as a glucose tolerance improving action for a mammal.

2. A method of treating a patient suffering from diabetes, which comprises administering to said patient an anti-diabetically effective amount of the substance of claim 1.

3. A process for preparing a biologically active substance consisting essentially of purified Islets-Activating Protein having insulin secretion promoting activity not less than 380 units/μg as well as glucose tolerance improving action for mammals, which comprises culturing at least one pathogenic strain of the microorganism Bordetella pertussis (Phase I or Phase II) in a culture medium therefor and collecting and purifying the cultured cells and/or culture medium by at least one method selected from the group consisting of the chromatographic method, the molecular sieve method, the electrophoretic method, and said biological method to recover the biologically active substance.

4. The process of claim 3, wherein said microorganism is Bordetella pertussis (phase I).

5. The process of claim 3, wherein said microorganism is Bordetella pertussis (phase II).

6. The process of claim 4 or 5, wherein said chromatographic method is a column chromatographic process which uses at least one column selected from the group consisting of hydroxy-apatite column, bead formed haptoglobin-agarose gel column, bead formed carboxymethyl-agarose gel column, covalently cross-linked allyl dextran/N,N'-methylene bisacrylamide column, bead formed concanavalin-agarose gel column, copolymerized acrylamide/N,N'-methylenebisacrylamide column, bead formed p-acetoxymercuryaniline-agarose gel column and bead formed Anti-IAP antibody-agarose gel column.

7. The process of claim 6, wherein said column chromatographic process uses a hydroxyapatite column and a bead formed haptoglobin-agarose gel column.

8. The process of claim 6, wherein said column chromatographic process uses a bead formed haptoglobin-agarose gel column and a covalently cross-linked allyl dextran/N,N'-methylene bisacrylamide column.

9. The process of claim 6, wherein said column chromatographic process uses a bead formed haptoglobin-agarose gel column and a bead formed carboxymethyl agarose gel column.

10. An anti-diabetic composition in dosage unit form, which comprises:

an anti-diabetically effective amount of a biologically active substance consisting essentially of purified Islets-Activating Protein having insulin secretion promoting action not less than 380 units/μg as well as glucose tolerance improving action for a mammal, obtained by culturing at least one pathogenic strain of the microorganism *Bordetella pertussis* (Phase I or Phase II) in a culture medium therefor and collecting and purifying from the cultured cells and/or culture medium by at least one method selected from the group consisting of the chromatographic method, the molecular sieve method, the electrophoretic method, and the biological method, to recover said biologically active substance having the following properties:

a molecular weight of 73,000±11,000 as determined by gel filtration;

a protein content as determined by Lowry's method of not less than 95% by weight;

the glucide content by the phenol—$H_2SO_4$ method of less than 2% by weight;

the lipid content being lower than the limit of detection;

percentile amino acid composition of the protein moiety (average ratio $\mu M/100 \mu M$) being: aspartic acid, 7.5–7.9; threonine, 6.8–7.8; serine 5.9–7.6; glutamic acid, 8.8–10.0; proline, 5.5–6.4; glycine, 8.7–9.6; alanine, 9.0–10.8; cysteine/2, 1.0–2.5; valine 6.5–7.6; methionine, 2.5–3.3; isoleucine, 3.6–4.6; leucine, 7.4–8.7; tyrosine, 5.1–6.8; phenylalanine, 3.7–4.5; lysine, 3.1–4.4; histidine, 0.9–1.5; and arginine, 6.1–6.6;

disc electrophoretic pattern: acrylamide (polyacrylamide) concentration, 7.5%; a 1N KOH—glacial acetic acid buffer (pH 4.3) disc electrophoresis of said substance giving a very sharp single band on the cathode side;

hydroxyapatite column chromatographic pattern:

said substance in 0.1 M phosphate buffer (pH 7.0) being adsorbed on said column and the adsorbed substance being eluted with 0.1 M phosphate buffer (pH 7.0) containing 0.5 M NaCl;

isoelectric point of pH 8.9±0.5; and optical rotation $[\alpha]_D^{25} = -29° \pm 5°$;

and a pharmaceutically acceptable carrier therefor.

* * * * *